United States Patent
Au-Yeung et al.

(10) Patent No.: US 10,018,623 B1
(45) Date of Patent: Jul. 10, 2018

(54) MOLECULAR PROBES FOR ASCORBATE DETECTION AND METHODS OF USE

(71) Applicant: The University of Hong Kong, Hong Kong (HK)

(72) Inventors: Ho Yu Au-Yeung, Taipo (HK); Zuo Hang Yu, Hong Kong (HK)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 15/453,169

(22) Filed: Mar. 8, 2017

(51) Int. Cl.
*C07F 1/08* (2006.01)
*G01N 33/52* (2006.01)
*G01N 33/82* (2006.01)

(52) U.S. Cl.
CPC .............. *G01N 33/52* (2013.01); *C07F 1/08* (2013.01); *G01N 33/82* (2013.01)

(58) Field of Classification Search
CPC ............ C07F 1/08; G01N 33/52; G01N 33/82
USPC ........................................................ 544/64
See application file for complete search history.

(56) References Cited

U.S. PATENT DOCUMENTS

| | | |
|---|---|---|
| 3,771,964 A | 11/1973 | Fader |
| 5,709,854 A | 1/1998 | Griffith-Cima |
| 6,129,761 A | 10/2000 | Hubbell |
| 6,858,229 B1 | 2/2005 | Hubbell |

FOREIGN PATENT DOCUMENTS

| | | |
|---|---|---|
| CN | 100510704 | 1/2008 |
| CN | 104267013 | 1/2015 |
| JP | 11326207 | 11/1999 |

OTHER PUBLICATIONS

Au-Yeung, et al., "Molecular imaging of labile iron(II) pools in living cells with a turn-on fluorescent probe", J. Am. Chem. Soc., 135(40)15165-73 (2013).
Ishii, et al., "Phthalocyanine-based fluorescence probes for detecting ascorbic acid: phthalocyaninatosilicon covalently linked to TEMPO radicals", Chem. Commun., 47:4932-4 (2011).
Liu, et al., "Interactions of nitroxide radicals with dendrimer-entrapped Au8-clusters: a fluorescent nanosensor for intracellular imaging of ascorbic acid", J. Mater. Chem. B, 3:191-7 (2015).
Maity, et al., "Reaction-based probes for Co(II) and Cu(I) with dual output modes: fluorescence live cell imaging", RSC Adv., 3:16788-94 (2013).
Song, et al., "Background-free in-vivo Imaging of Vitamin C using Time-gateable Responsive Probe", Scientific Reports, 5:14194 (2015).
Vislisel, et al., "A simple and sensitive assay for ascorbate using a plate reader", Anal Biochem., 365(1):31-9 (2007).

*Primary Examiner* — Kahsay Habte
(74) *Attorney, Agent, or Firm* — Pabst Patent Group LLP

(57) ABSTRACT

Described are metal complexes for the selective detection of ascorbic acid or ascorbate. The metal complexes act as molecular sensors, and are useful in detecting ascorbate in live biological samples, commercial samples, or both. The selective ascorbate sensing involves an ascorbate-selective bond cleavage reaction. The bond cleavage is not limited to the construction of molecular sensors, but also includes other stimuli-responsive materials, i.e., materials that adopt a physical state, such as gel formation, upon ascorbate-selective bond cleavage of the metal complexes.

37 Claims, 9 Drawing Sheets

| YOU·C1000 (lemon juice) | Ascorbate content in sample (1000-fold dilution) µM (n=4) | Recovery (n=4) |
|---|---|---|
| No spike | 6.4 ± 0.25 | - |
| Spike 1 (1 µM ascorbate) | 7.3 ± 0.17 | 96.8% ± 4.6% |
| Spike 2 (2 µM ascorbate) | 8.4 ± 0.22 | 99.0% ± 4.7% |

Figure 7

MOLECULAR PROBES FOR ASCORBATE DETECTION AND METHODS OF USE

FIELD OF THE INVENTION

The disclosed invention is generally in the field of molecular sensors, and specifically in the area of selective detection of ascorbate.

BACKGROUND OF THE INVENTION

Ascorbic acid, ascorbate (Asc), also known as vitamin C, is an important antioxidant that plays an essential role in the biosynthesis of numerous bioactive substances. Ascorbate is a water soluble and is essential for human health. Ascorbic acid and its sodium, potassium, and calcium salts are widely used in many fields, serving as an antioxidant in food, animal feed, beverages, cosmetics, and pharmaceutical formulations (Liu, et al., J. Agric. Food Chem. 2016, 64, 371-380). In humans, ascorbate has to be obtained from diet and its deficiency leads to diseases such as scurvy (Padayatty, S J, et al., J Am Coll Nutr. 2003 February; 22(1): 18-35). Ascorbate is involved in many biochemical processes including cellular redox regulations and enzymatic reactions, and is implicated in body defence and several different diseases (Arrigoni, O, et al., Biochim. Biophys. Acta, Gen. Subj. 2002, 1569, 1-9). Ascorbate is also very important in plants and is involved in crucial biochemical processes such as photosynthesis and respiration (Smirnoff, N., et al., Crit. Rev. Plant Sci. 2000, 19, 267-290). Due to its antioxidant properties and nutritional value, ascorbate is also a common additive in foods and commercial products. Numerous methods for detecting ascorbic acid have been developed, including titration with an oxidizing agent, electrochemistry, spectrophotometry, chromatography and chemiluminescence, enzymology, and capillary electrophoresis.

Several studies employ electrochemical methods as the detection strategy towards ascorbic acid, which include WO2014041465, CN103604849, CN103399056, CN101587094, CN101059474, U520070074971/EP1606631/WO2004083868, WO2015099546, WO2009021907, U.S. Pat. No. 7,598,546 and CN102564963. For electrochemical detection, an electric current is generated resulting from the oxidation reaction of ascorbic acid at the electrode. The various patents listed above describe different electrode material for the detection. In general, the electrochemical sensor is vulnerable to interference from other redox active chemicals in the biological matrix, because of their similar electric potential.

Other studies describe high-performance liquid chromatography (HPLC) detection and quantification for ascorbate (Novakova and Solich, TrAC Trends in Analytical Chemistry 2008, 27(10), 942-958; and Pastore, et al., Rapid Commun. Mass. Spectrom. 2001, 15(22), 2051-2057). In HPLC, different components in the sample are separated by a column and detected by UV or other detectors. HPLC in general has a large dynamic range and good accuracy. However, analysis time is long (10-45 min for one sample) and expensive instrument with technical skills are required.

Additional investigations describe using optical methods for ascorbate detection. In CN100510704C, gold nanoparticle that displays change in fluorescence properties is used to detect ascorbate. In CN104267013, a mixture of graphene quantum dot and potassium chromate is employed to detect ascorbate, which restores the fluorescence quenched by the salt. Vislisel, et al., Analytical Biochemistry 2007, 365(1), 31-39 describes condensation of dehydroascorbate, an oxidation product of ascorbate, with o-phenylenediamine (OPDA) to form a fluorescent product for the fluorescent detection of ascorbate. Tempol, a nitroxide radical, is used as the oxidant. In JP11326207, the same OPDA condensation strategy is used, but the degree of polarization of fluorescence is measured instead of the emission intensity. Song, et al., Scientific Reports 2015, 5, 14194 also uses a nitroxide radical as the oxidizing partner with ascorbate to control the emission properties of a lanthanide. The fluorophore with the nitroxide radical only has weak fluorescence and ascorbate reduction of the radical restores and enhances the emission of the fluorophore. Ishii, et al., Chem. Commun. 2011, 47, 4932-4934 ("Ishii"), also uses a nitroxide radical as the ascorbate reacting/responding unit which is linked to and alters the emission property of a phthalocyaninatosilicon. Liu, et al., J. Mater. Chem. B 2015, 3, 191-197 describe emission of gold nanoclusters $Au_8$, which was quenched by TEMPO (a nitroxide radical) derivatives upon which addition of ascorbate restores the emission by oxidizing the TEMPO with the vitamin.

U.S. Pat. No. 4,303,409 describes a colorimetric analysis based on metal complexes of different colors. Redox reaction between the metal and ascorbate changes the color of the system and thus allows colorimetric detection of ascorbate. U.S. Pat. No. 3,771,964 describes another colorimetric assay based on a phosphomolybdate salt which changes color in the presence of ascorbate. U.S. Pat. No. 6,153,399 also uses ascorbate oxidase to oxidize ascorbate in the presence of chromogen and peroxidase, and ascorbate concentration is determined by monitoring changes in absorbance.

In DE4304728, ascorbic acid is detected by using a photochemiluminescence (PCL) measurement system. Autooxidation of luminol is inhibited by ascorbate and the lag phase of photochemiluminescence is correlated with the ascorbate concentration.

Au-Yeung, et al., J. Am. Chem. Soc. 2013, 135(40), 15165-15173 ("Au-Yeung") describes molecular imaging of labile iron(II) pools in living cells. Ascorbic acid is used to increase the pool of labile iron(II) ions. The release of a fluorophore is triggered by the presence of free metal ions and oxygen. Maity, et al., RSC Adv. 2013, 3, 16788-16794 ("Maity") describes reaction based molecular probes for selective colorimetric and fluororimetric detection of Co(II) and Cu(I). Binding of these metals to the probes triggers the release of a fluorophore. Au-Yeung and Maity detect the presence of metal ions and not ascorbic acid.

Among the ascorbic acid detection methods described above, only few are applicable in the imaging of live cell: Au-Yeung, Maity, Liu and Ishii. Other methods that require sample pretreatment and preparation (e.g. HPLC), the use of additional reagents (e.g. the OPDA method) are not applicable in live biological sample such as living cells. In addition, the use of nitroxide radical as the ascorbate responding functional group in many of the above examples of fluorescent/colorimetric/luminescent methods pose selectivity problems as other radical/paramagnetic species (e.g. transition metals)/reducing agents could also react with the nitroxide radical. Accordingly, there remains a need to develop analytical tools that can efficiently detect ascorbate, and in particular, in live biological samples such as cells.

Therefore, it is an object of the present invention to provide enhanced molecular sensors.

It is another object of the present invention to provide molecular sensors that selectively detect ascorbate or ascorbic acid, and in particular, in commercial samples, live biological samples, or a combination thereof.

It is another object of the present invention to provide metal complexes that selectively detect ascorbate or ascorbic acid.

SUMMARY OF THE INVENTION

Metal complexes for the selective detection, quantification, or both, of ascorbic acid or a salt thereof are described. The metal complexes act as molecular sensors, also known as molecular probes. The molecular sensors are weakly emissive, i.e., show no emission or substantially low emission of electromagnetic radiation, but can be converted by a chemical reaction with a compound, such as ascorbic acid or a salt thereof, into forms with enhanced emission properties upon excitation, for example via photo excitation. The sensors contain a covalent bond between a ligand and a diagnostic agent (such as a fluorophore), therapeutic agent, prophylactic agent, or a combination thereof, which is cleaved in the presence of ascorbic acid or a salt thereof to release the fluorophore with enhanced fluorescent properties. Preferably, the metal complexes do not release the fluorophore in the presence of oxygen or in reducing conditions, such as the in presence of glutathione within cells. Preferably, the release of the fluorophore from the metal complexes is triggered selectively by ascorbate, but not by one or more free metal ions or glutathione. Upon reaction with ascorbate under aerobic conditions, a C—O ether bond between a ligand and a diagnostic agent (such as a fluorophore), therapeutic agent, prophylactic agent, or a combination thereof, occurs. The active, luminescent fluorophore is released and is accompanied by a fluorescence enhancement. The fluorescence enhancement can be used as a reporter for the presence of ascorbate, its level in the sample, or both. The bond cleavage is not limited to the construction of molecular sensors, but also includes other stimuli-responsive materials, i.e., materials that adopt a physical state, such as gel formation, upon ascorbate-selective bond cleavage of the metal complexes.

The metal complexes have the formula:

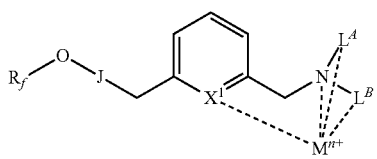

Formula I wherein:
M is a transition metal, preferably copper;
n is an integer between 1 and 7, inclusive, preferably 2;
J is a single bond;
$R_f$ includes a diagnostic, therapeutic, or prophylactic agent, preferably a diagnostic agent, such as a fluorophore;
$X^1$ is preferably N or CH;
$L^A$ is preferably $CH_2NR^1R^2$, $CH_2OR^3$, $CH_2COOR^4$, $CH_2SR^5$,

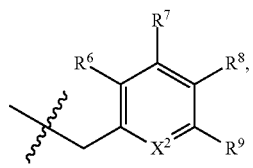

or

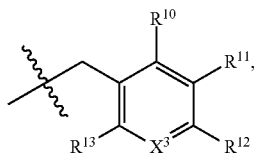

preferably, $R^1$-$R^5$ are independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, preferably, $R^6$-$R^{21}$ are independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, F, Cl, Br, I, CN, OH, OMe, $NH_2$, or $NMe_2$, preferably $X^2$ and $X^3$ are N or CH;

$L^B$ is preferably $CH_2N(R^1R^2)$, $CH_2OR^3$, $CH_2COOR^4$, $CH_2SR^5$,

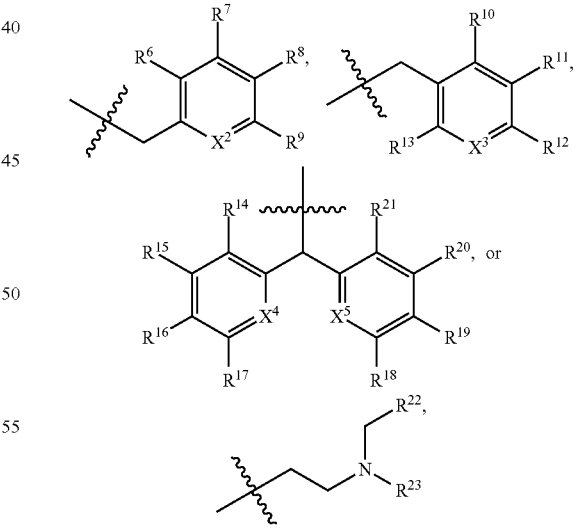

preferably $R^1$-$R^5$ are independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, or 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, preferably, $R^6$-$R^{21}$ are independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, F, Cl, Br, I, CN, OH, OMe, $NH_2$, or $NMe_2$, preferably, $R^{22}$ and $R^{23}$ are independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, F, Cl, Br, I, CN, OH, OMe, $NH_2$, or $NMe_2$, $NEt_2$, 2-pyridyl, methylthio, ethylthio, COOH, $COOR^{25}$, wherein $R^{25}$ can be unsubstituted alkyl, substituted alkyl, unsubstituted aryl, or unsubstituted aryl, preferably $X^2$, $X^3$, $X^4$, and $X^5$ are N or CH.

Variations in $R_f$, such as by using different fluorophores during chemical synthesis, result in ascorbate fluorescent sensors with different photophysical properties. In particular, ascorbate sensors have different emission colors via the use a variety of fluorophores including fluorescein (green emitting), resorufin (orange emitting), coumarin (blue emitting) and hydroxybenzothiazole (ratiometric).

BRIEF DESCRIPTION OF THE DRAWINGS

FIG. 2A shows fluorescence response of a 5-04 solution of pAP1 upon reaction of 20 eq Asc for 30 mins ($\lambda_{ex}$=470 nm). Spectra were acquired in deionized water. FIG. 2B shows relative emission intensity of pAP1 in different buffers (pH 7.4, 50 mM) in the presence of Asc. FIG. 2C shows selectivity of a 5-04 solution of pAP1 against 20 eq of various biological reductants. FIG. 2D shows selectivity of pAP1 against 20 eq of various amino acids. FIG. 2E shows selectivity of a 5-04 solution of pAP1 against 20 eq of various vitamins. FIG. 2F shows selectivity of a 5-04 solution of pAP1 against 20 eq of various metal ions. FIG. 2G shows selectivity of a 5-04 solution of pAP1 against 20 eq of sugars and common food additives. FIG. 2H shows selectivity of a 5-μM solution of pAP1 against various reactive oxygen species.

FIG. 7 shows a determination of ascorbate content in the commercial lemon juice YOU•C1000 using pAP1.

DETAILED DESCRIPTION OF THE INVENTION

I. Definitions

Figure 1:
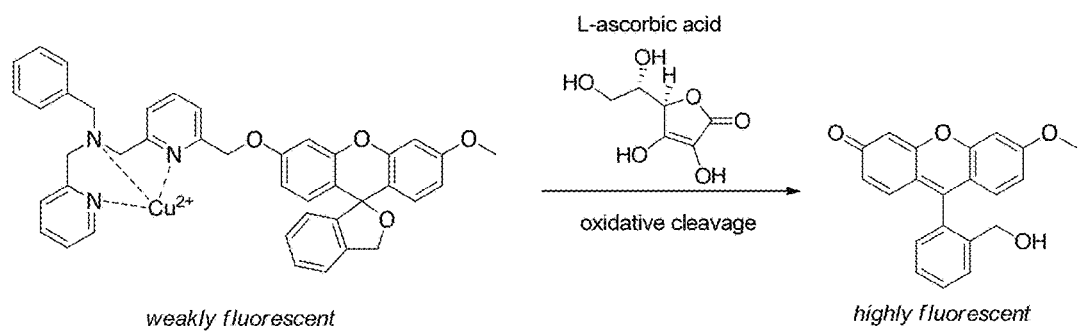
FIG. 1 depicts structures and reaction chemistry of a probe containing AP1 (pAP1).

It is to be understood that the disclosed compounds, compositions, and methods are not limited to specific synthetic methods, specific analytical techniques, or to particular reagents unless otherwise specified, and, as such, may vary. It is also to be understood that the terminology used herein is for the purpose of describing particular forms and embodiments only and is not intended to be limiting.

The term "substantially low emission," as relates to fluorescence, describes a fluorescence intensity that is at background levels or less than 10% of the fluorescence of a released fluorophore, as measured using a fluorometer. Useful examples of substantially low emission include fluorescence intensity that is less than 5%, less than 4%, less than 3%, less than 2%, less than 1%, less than 0.5%, less than 0.1%, or 0% of the fluorescence of a released fluorophore, as measured using a fluorometer.

"Ascorbic acid," and "ascorbate" are used interchangeably to refer to the molecular structure of vitamin C (ascorbic acid) or a salt thereof (ascorbate).

"Metallic complex," "metal complex," and "organometallic complex" are used interchangeably to refer to a compound containing a central metal atom and one or more compounds chelating the central metal.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Alkyl," as used herein, refers to the radical of saturated aliphatic groups, including straight-chain alkyl groups, branched-chain alkyl, cycloalkyl (alicyclic), alkyl substituted cycloalkyl groups, and cycloalkyl substituted alkyl. In preferred forms, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Alkyl includes methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred forms, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —$CF_3$, —$CH_2$—$CF_3$, —$CCl_3$); —CN; —$NCOCOCH_2CH_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

The terms "alkoxyl" or "alkoxy," "aroxy" or "aryloxy," generally describe compounds represented by the formula —OR$^v$, wherein R$^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits. A "lower alkoxy" group is an alkoxy group containing from one to six carbon atoms.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkenyl" as used herein is a hydrocarbon group of from 2 to 24 carbon atoms and structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "aryl" as used herein is any $C_5$-$C_{26}$ carbon-based aromatic group, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, including, but not limited to, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics".

"Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quartemized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quartemized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quartemized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

"Carbonyl," as used herein, is art-recognized and includes such moieties as can be represented by the general formula:

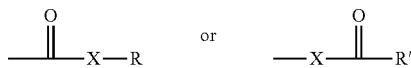

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R", or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —(CH$_2$)$_m$—R"; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

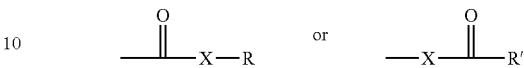

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quartemized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "carboxyl" is as defined above for the formula

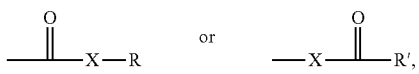

and is defined more specifically by the formula —R$^{iv}$COOH, wherein R$^{iv}$ is an alkyl, alkenyl, alkynyl, cycloalkyl, heterocyclyl, alkylaryl, arylalkyl, aryl, or heteroaryl. In preferred forms, a straight chain or branched chain alkyl, alkenyl, and alkynyl have 30 or fewer carbon atoms in its backbone (e.g., C1-C30 for straight chain alkyl, C3-C30 for branched chain alkyl, C2-C30 for straight chain alkenyl and alkynyl, C3-C30 for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in R$^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenoxy" is art recognized, and refers to a compound of the formula —OR$^v$ wherein R$^v$ is (i.e., —O—C$_6$H$_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to —S—$C_6H_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "amide" or "amido" are used interchangeably, refer to both "unsubstituted amido" and "substituted amido" and are represented by the general formula:

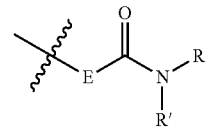

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide. In preferred forms, R and R' each independently represent a hydrogen atom, substituted or unsubstituted alkyl, a substituted or unsubstituted alkenyl, or —$(CH_2)_m$—R'''. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

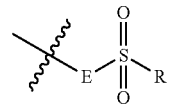

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

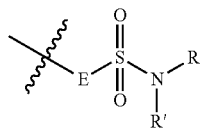

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide.

The term "phosphonyl" is represented by the formula

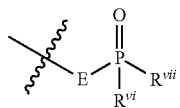

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, R$^{vi}$ and R$^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, R$^{vi}$ and R$^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phosphoryl" defines a phosphonyl in which E is absent, oxygen, alkoxy, aroxy, substituted alkoxy or substituted aroxy, as defined above, and independently of E, R$^{vi}$ and R$^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, R$^{vi}$ and R$^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof. When two or more heteroaryls are involved, the chemical moiety can be referred to as a "polyheteroaryl."

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. When two or more heteroaryls are involved, the chemical moiety can be referred to as a "substituted polyheteroaryl."

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "urethane" as used herein is represented by the formula —OC(O)NRR', where R and R' can be, independently, hydrogen, an alkyl, alkenyl, alkynyl, aryl, aralkyl, cycloalkyl, halogenated alkyl, or heterocycloalkyl group described above.

The term "silyl group" as used herein is represented by the formula —SiRR'R", where R, R', and R" can be, independently, hydrogen, an alkyl, alkenyl, alkynyl, aryl, aralkyl, cycloalkyl, halogenated alkyl, alkoxy, or heterocycloalkyl group described above.

The terms "hydroxyl" and "hydroxy" are used interchangeably and are represented by —OH.

The terms "thiol" and "sulfhydryl" are used interchangeably and are represented by —SH.

The term "oxo" refers to =O bonded to a carbon atom.

The terms "cyano" and "nitrile" are used interchangeably to refer to —CN.

The term "nitro" refers to —$NO_2$.

The term "phosphate" refers to —O—$PO_3$.

The term "azide" or "azido" are used interchangeably to refer to —$N_3$.

The disclosed compounds and substituent groups, can, independently, possess two or more of the groups listed above. For example, if the compound or substituent group is a straight chain alkyl group, one of the hydrogen atoms of the alkyl group can be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group comprising an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

The compounds and substituents can be substituted with, independently, with the substituents described above in the definition of "Substituted."

II. Compounds

Described herein, are a class of metallic complexes containing a ligand, diagnostic, therapeutic, and/or prophylactic agent, in which a covalent linkage or bond between the ligand and the diagnostic, therapeutic and/or prophylactic agent is cleaved in the presence of a stimulus. The diagnostic agent can be a dye. The stimulus can be compound, such as ascorbate. In particular, a class of copper coordination complexes in which the covalent linkage between metal coordination complex and any responsive unit may be cleaved upon reaction with ascorbate. Cleavage of the covalent linkage or bond can release a luminescent reporter (such as a fluorophore) to generate a signal to be detected. The signal can be visible light. The fluorophore can non-emissive or substantially non-emissive when it is linked to the metal complex. Upon reaction with ascorbate, an $O_2$-dependent oxidative bond cleavage is triggered to break the linkage between the metal complexes and the fluorophore, releasing the fluorescent reporter in its emissive or enhanced emissive form to result in an increase in fluorescence.

A variety of ligand structures and different fluorophores and methods of using and making the same are contemplated by the present invention. In certain embodiments, the ligands form coordination complexes with various metal ions, in particular copper(II), in which the addition of ascorbate will trigger the release of a fluorophore.

A. Metallic Complexes

Disclosed are metallic complexes or compounds having the formula:

Formula I

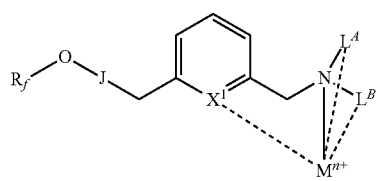

wherein:

M can be a transition metal;

n can be an integer between 1 and 7, inclusive;

J can be a single bond;

$R_f$ includes a diagnostic, therapeutic, or prophylactic agent;

$L^A$ and $L^B$ can be independently $CH_2N(R^1R^2)$, $CH_2OR^3$, $CH_2COOR^4$, $CH_2SR^5$,

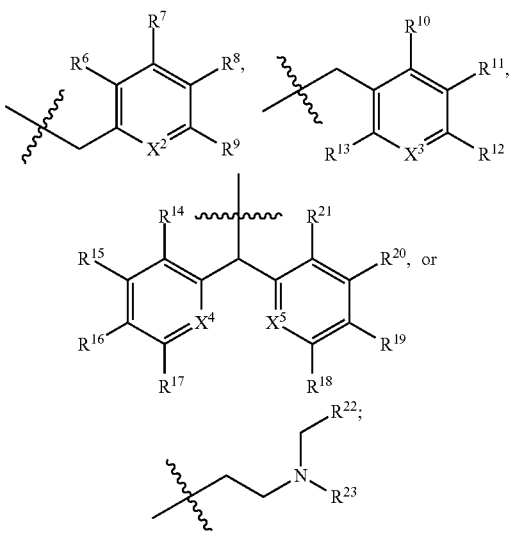

$X^1$, $X^2$, $X^3$, $X^4$, and $X^5$ can be independently N or $CR^{24}$; and $R^1$-$R^{24}$ can be independently hydrogen, unsubstituted alkyl, substituted alkyl, unsubstituted aryl, substituted aryl, unsubstituted polyaryl, substituted polyaryl, halogen, cyano, hydroxyl, unsubstituted alkoxy, substituted alkoxy, unsubstituted amino, substituted amino, unsubstituted dialkyl amine, substituted dialkyl amine, unsubstituted heteroaryl, substituted heteroaryl, unsubstituted polyheteroaryl, substituted polyheteroaryl, unsubstituted alkylthio, substituted alkylthio, unsubstituted carboxyl, substituted carboxyl, unsubstituted ester, substituted ester, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl.

In some forms, the presence of ascorbic acid, or a salt thereof, triggers the cleavage of J. The ascorbic acid, or salt thereof, can act as a reducing agent that reduces the metal ion to a lower oxidation state, such as $Cu^{2+}$ to $Cu^+$, as well as any metal-bound reactive oxygen species generated from the reduced metal complexes upon reaction with oxygen to result in a species that cleaves the ether bond, J. It was observed that the oxidized form of ascorbic acid—dehydroascorbate—does not result in the cleavage of ether bond, J. Further, it was discovered that, in the absence of ascorbic acid, the metal ion in its lower oxidation state does not give rise to bond cleavage. This was exemplified using probes containing $Cu^{2+}$.

In some forms, at least one of $X^1$, $L^A$, or $L^B$ is nitrogen, or contains a nitrogen atom, as valency permits, coordinating with $M^{n+}$.

In some forms, the metallic complexes of Formula I have the formula:

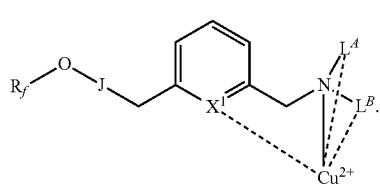

Formula II

In some forms, the diagnostic agent can be a dye. The dye can be a fluorescent dye, a chemiluminescent dye, a bioluminescent dye, a phosphorescent dye, or a combination thereof.

In some forms, $X^1$, $X^2$, $X^3$, $X^4$, and $X^5$ can be independently N or CH.

In some forms, $L^A$ can be $CH_2NR^1R^2$, $CH_2OR^3$, $CH_2COOR^4$, $CH_2SR^5$,

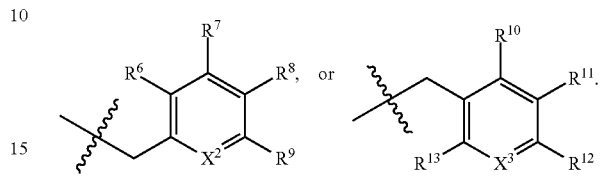

In some forms of $L^A$, $R^1$-$R^{13}$ can be independently hydrogen, unsubstituted alkyl, substituted alkyl, unsubstituted aryl, unsubstituted aryl, halogen, cyano, hydroxyl, unsubstituted alkoxy, substituted alkoxy, unsubstituted amino, substituted amino, unsubstituted dialkyl amine, or substituted dialkyl amine. Preferably, $R^1$-$R^5$ are independently hydrogen, unsubstituted alkyl, substituted alkyl, unsubstituted aryl, or unsubstituted aryl. Most preferably, $R^1$-$R^5$ can be independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, or 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. In some forms of $L^A$, $R^6$-$R^{21}$ can be independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, F, Cl, Br, I, CN, OH, OMe, $NH_2$, or $NMe_2$.

In some forms, $L^B$ can be $CH_2N(R^1R^2)$, $CH_2OR^3$, $CH_2COOR^4$, $CH_2SR^5$,

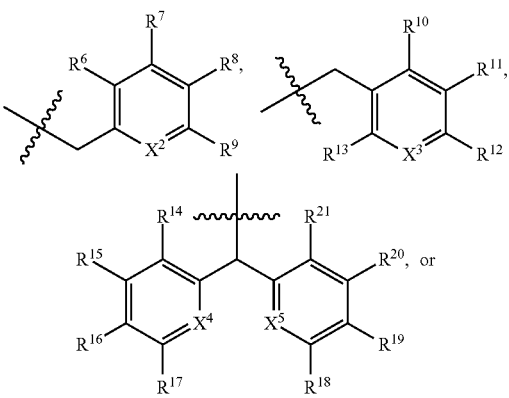

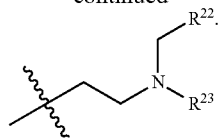

In some forms of $L^B$, $R^1$-$R^{23}$ are independently hydrogen, unsubstituted alkyl, substituted alkyl, unsubstituted aryl, substituted aryl, halogen, cyano, hydroxyl, unsubstituted alkoxy, substituted alkoxy, unsubstituted amino, substituted amino, unsubstituted dialkyl amine, substituted dialkyl amine, unsubstituted heteroaryl, substituted heteroaryl, unsubstituted alkylthio, substituted alkylthio, unsubstituted carboxyl, substituted carboxyl, unsubstituted ester, or substituted ester. Preferably, $R^1$-$R^5$ can be independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Preferably, wherein $R^6$-$R^{21}$ can be independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, F, Cl, Br, I, CN, OH, OMe, $NH_2$, or $NMe_2$. Preferably, $R^{22}$ and $R^{23}$ can be independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, F, Cl, Br, I, CN, OH, OMe, $NH_2$, or $NMe_2$, $NEt_2$, 2-pyridyl, methylthio, ethylthio, COOH, $COOR^{25}$, wherein $R^{25}$ can be unsubstituted alkyl, substituted alkyl, unsubstituted aryl, or substituted aryl.

In some forms, the metal complex is selected from:

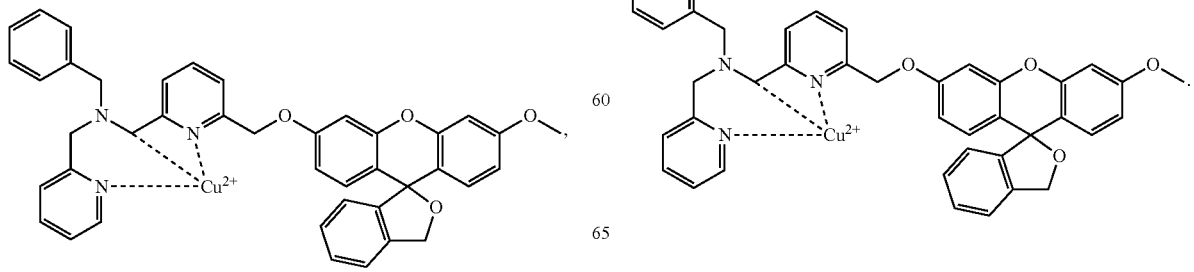

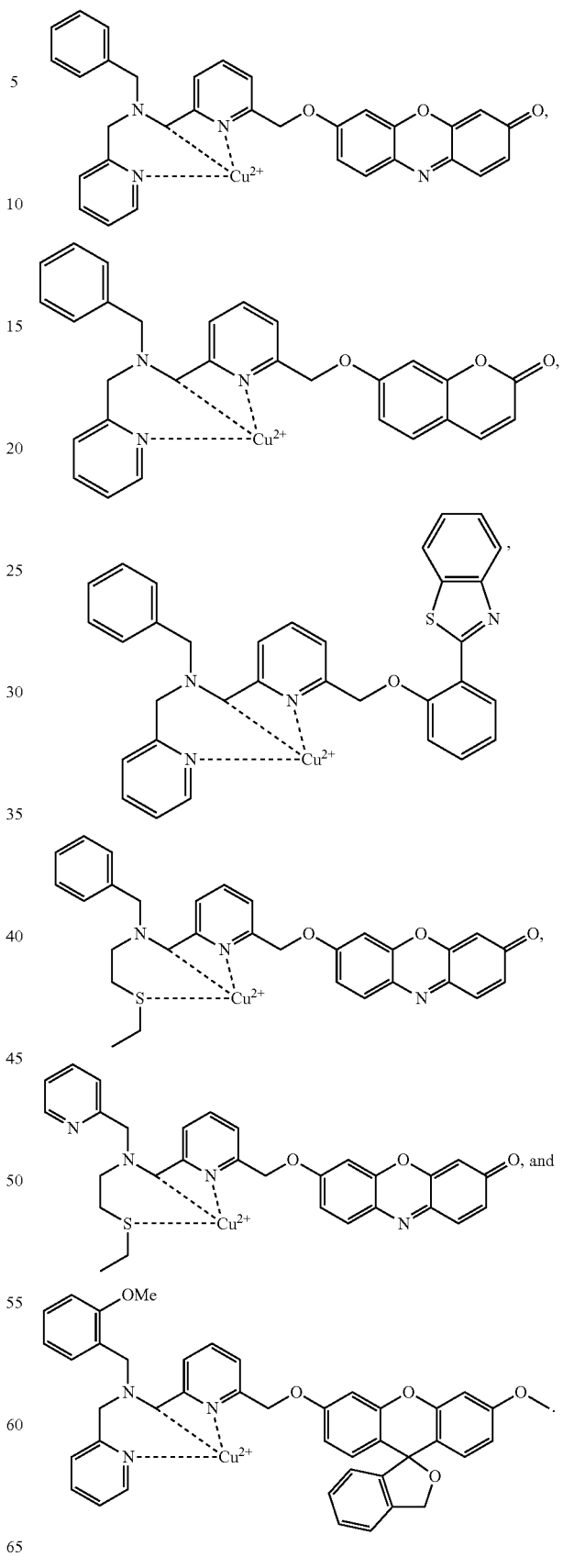

In some forms, the compounds have the formula:

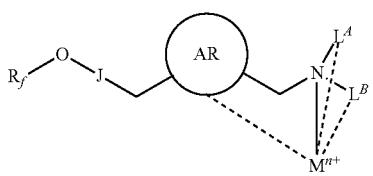

Formula IA wherein:

AR is unsubstituted aryl, substituted aryl, unsubstituted polyaryl, substituted polyaryl, unsubstituted heteroaryl, substituted heteroaryl, unsubstituted polyheteroaryl, substituted polyheteroaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl; and $R_f$, J, $L^A$, $L^B$, M, and n are as defined for any of the compounds described above.

B. Ligand- and Diagnostic, Therapeutic, and/or Prophylactic Agent Conjugates

Also described, are ligand- and diagnostic, therapeutic, and/or prophylactic agent conjugates.

In some forms, the conjugate is a ligand-diagnostic agent conjugate. In some forms, the ligand-diagnostic agent has the formula:

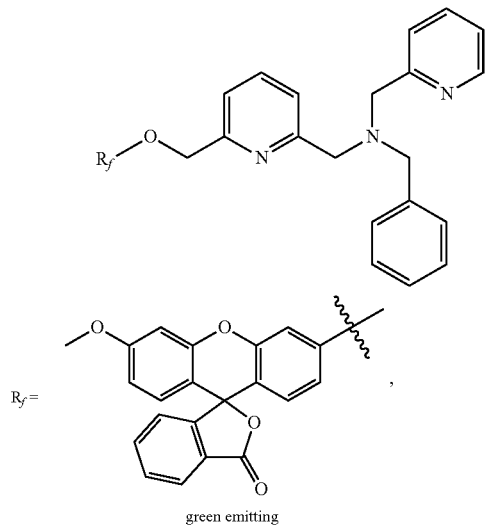

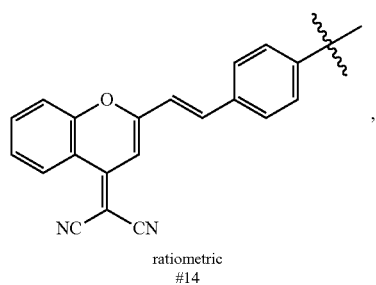

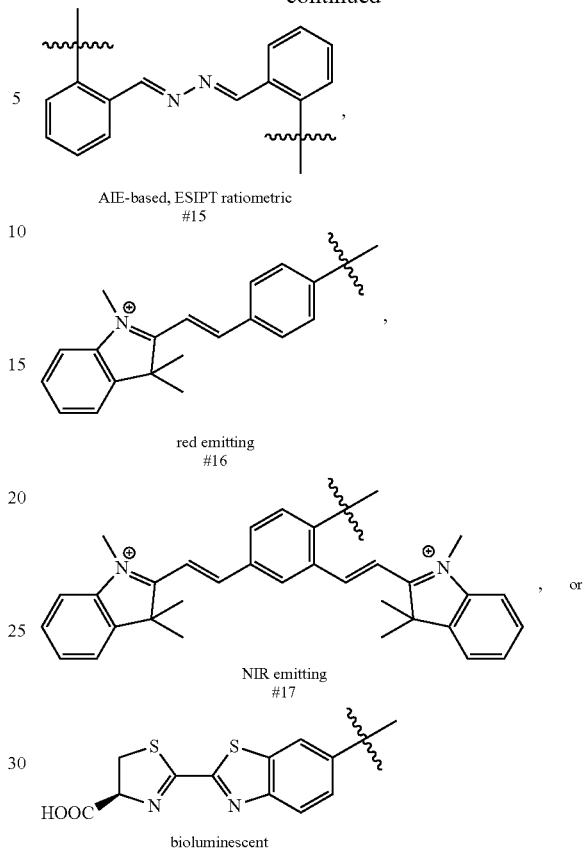

In some forms, the ligand-diagnostic agent conjugate has the formula:

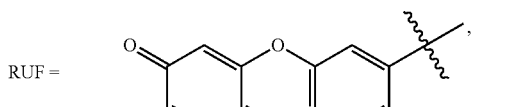

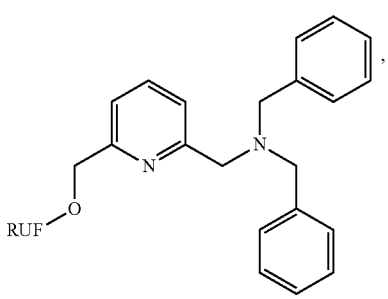

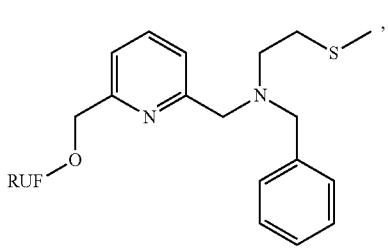

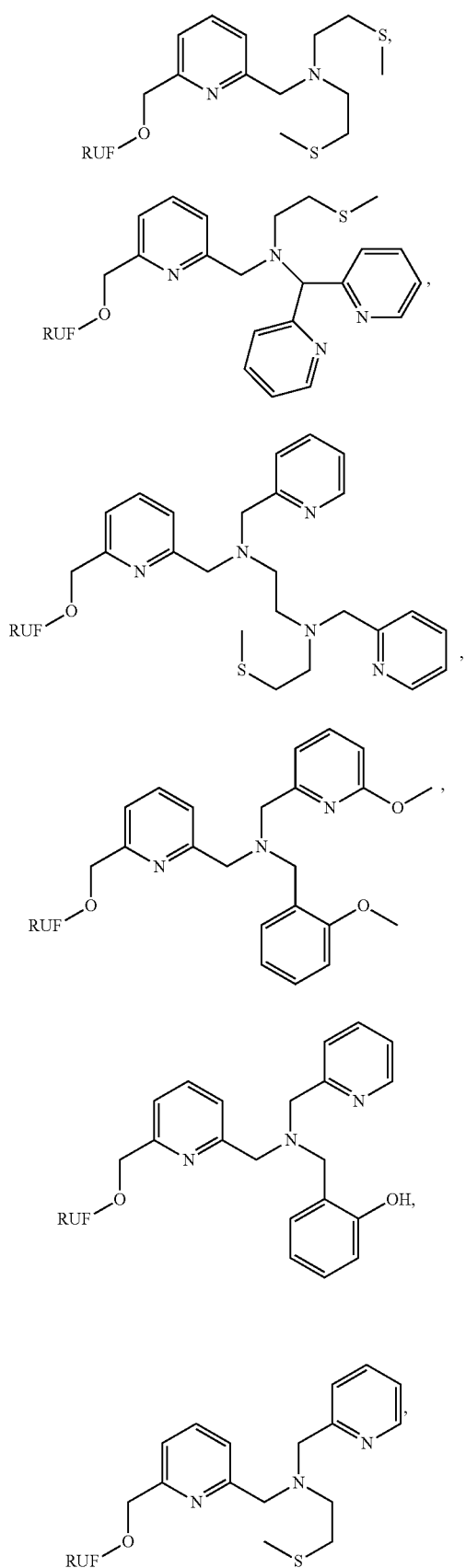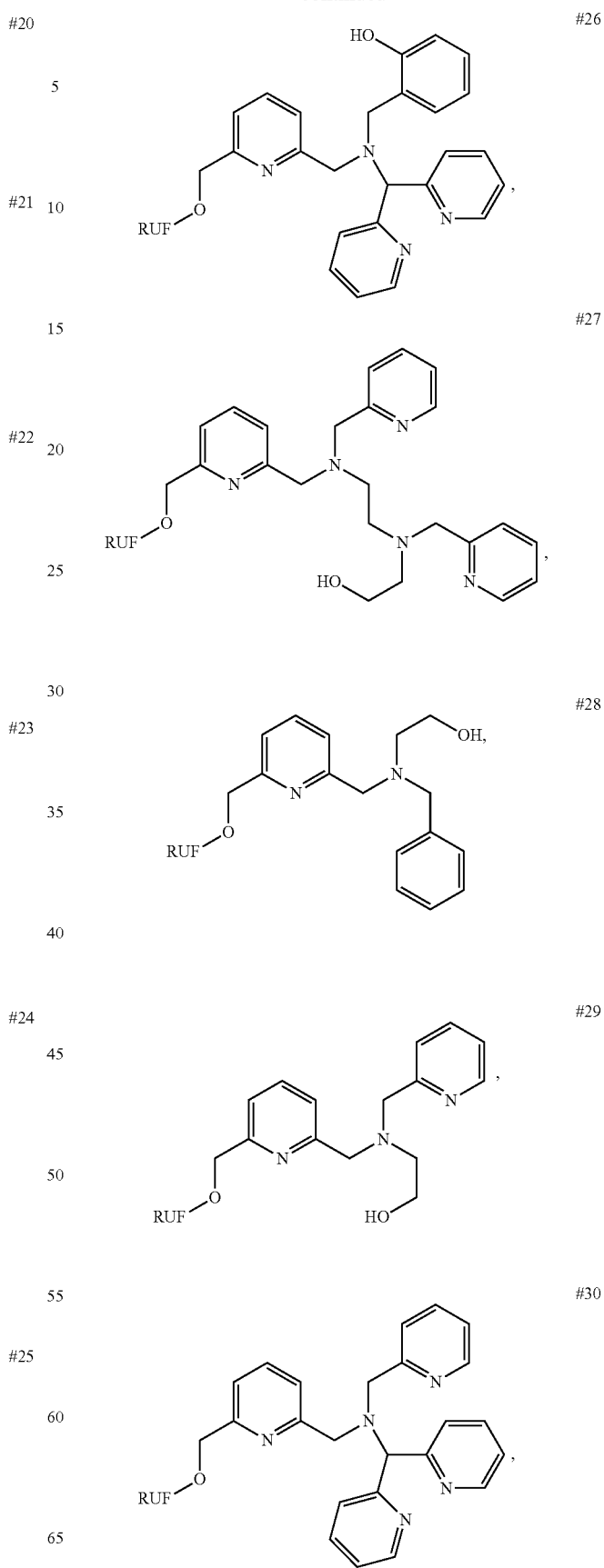

-continued
31
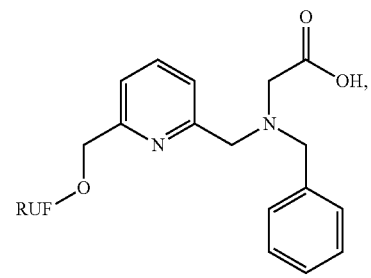
32
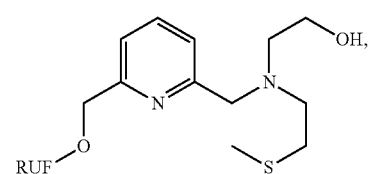
33
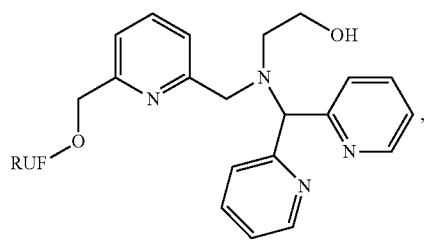
34
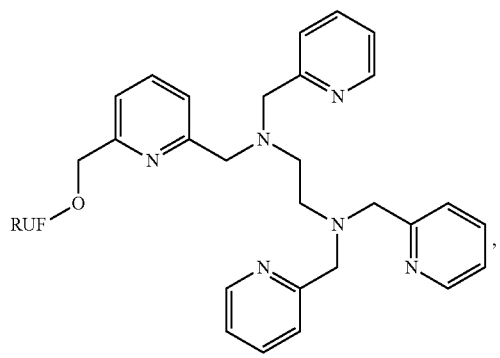
or
35
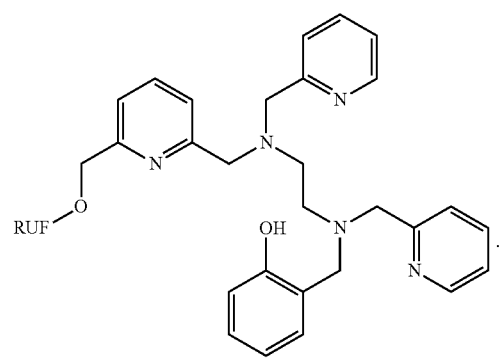
In some forms, the ligand-diagnostic agent conjugate has the formula:
2
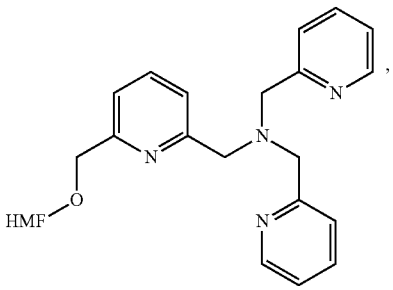
3
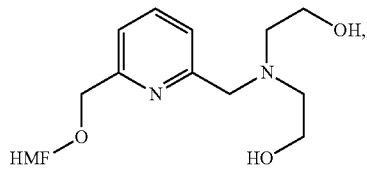
4
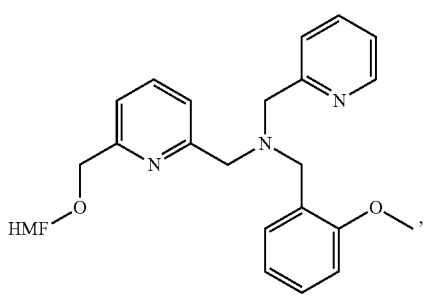
5
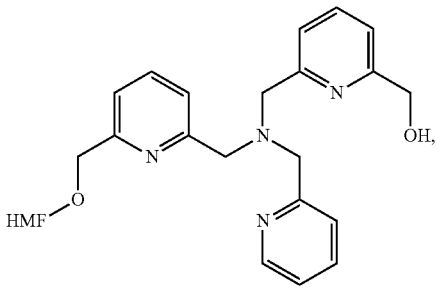
6
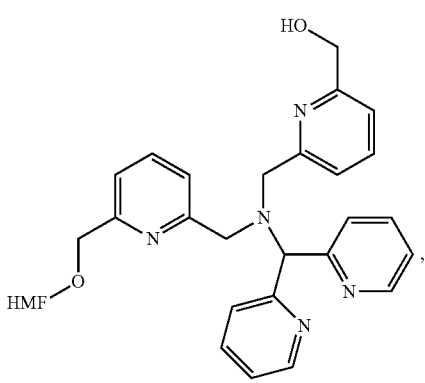

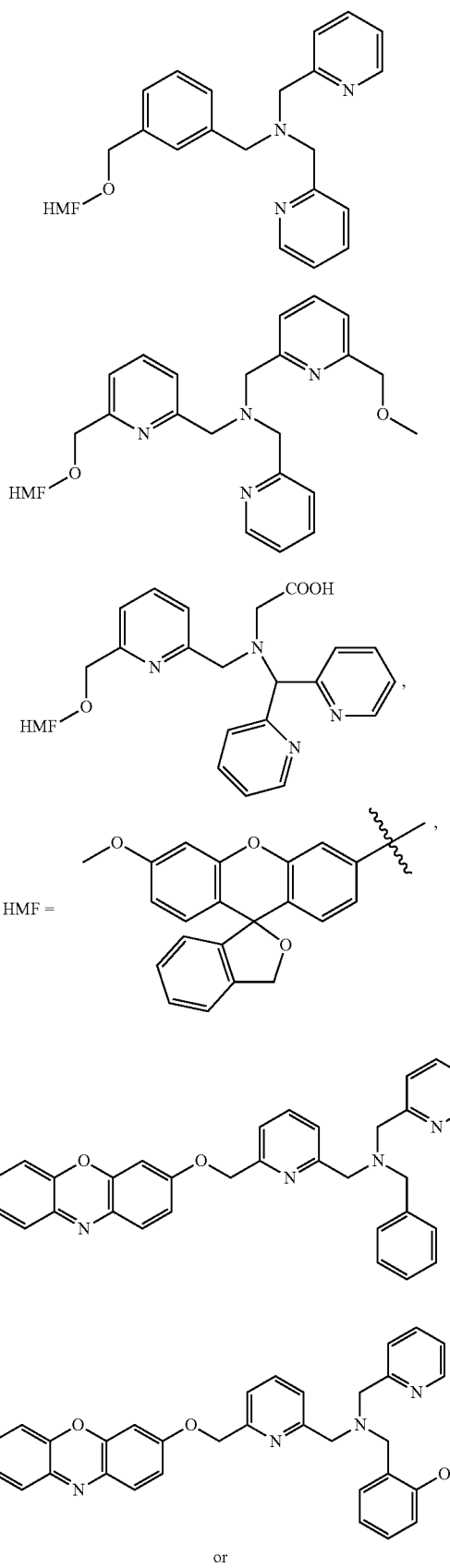

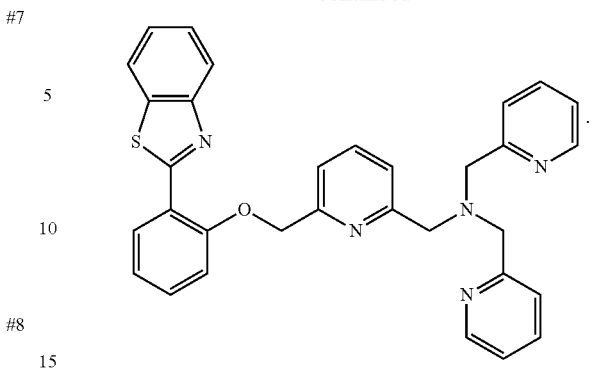

Also contemplated are ligand-therapeutic agent conjugates, i.e., $R_f$ is a therapeutic agent. The therapeutic agent can be a small molecule. "Small molecule" as relates to therapeutic agent, refers to a molecule with a molecular weight equal to or less than 2,000 Da.

Also contemplated are conjugates in which $R_f$ includes a compound that forms a gel upon ascorbate-triggered cleavage of a bond between the compound and the ligand. In some forms, $R_f$ can be a compound, such as polymer, that forms a hydrogel. In some forms, the compound optionally includes a diagnostic, therapeutic, or prophylactic agent. Examples of polymers that can form gels include, but are not limited to, polysaccharides such as alginate, polyphosphazines, poly(acrylic acids), poly(methacrylic acids), poly(alkylene oxides), poly(vinyl acetate), polyvinylpyrrolidone (PVP), and copolymers and blends of each. See, for example, U.S. Pat. Nos. 5,709,854, 6,129,761 and 6,858,229. In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups and sulfonic acid groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Preferably, the polymers that can form gels are biocompatible, biodegradable, or a combination thereof.

In some forms, $R_f$ can be a small molecule gelator containing one or more groups that can cross-link, covalently, non-covalently, or both, to form a gel. Suitable groups that can cross-link are known in the art. The groups can be selected from, for example, a hydroxyl, carboxyl, thiol, and amino groups. In some forms, the small molecule gelator can be masked by the complex such that the group cannot participate in the formation of a gel, but the ascorbate-triggered release of the unmasked gelator can expose the group in the gelator and result in the formation of gel.

C. Dyes

In some forms, the diagnostic agent can be a dye that has the formula:

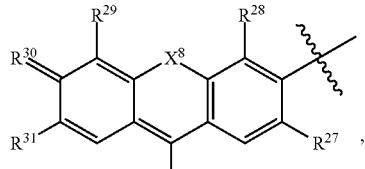

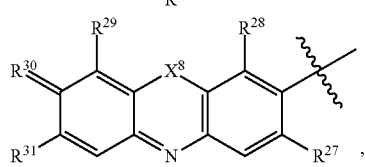

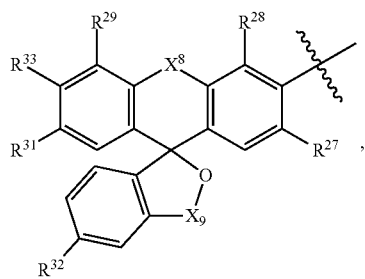

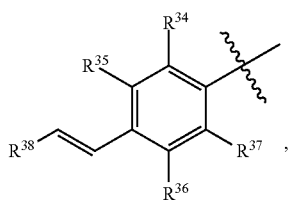

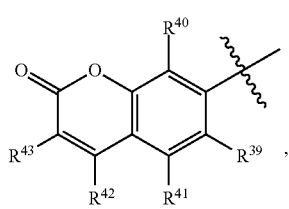

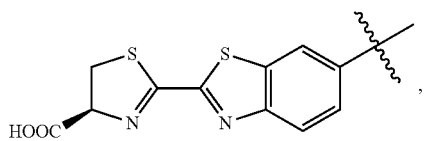

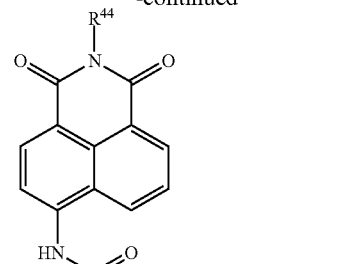

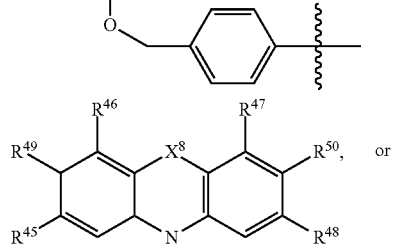

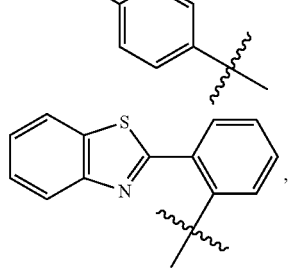

wherein:

$X^8$ can be O, S, Se, Te, $C(R^{52}R^{53})$, $Si(R^{52}R^{53})$, or $B(R^{52}R^{53})$;

$X^9$ can be $CH_2$, or C(O); and $R^{26}$-$R^{53}$ can be independently hydrogen, unsubstituted alkyl, substituted alkyl, unsubstituted aryl, substituted aryl, unsubstituted polyheteroaryl, substituted polyheteroaryl, halogen, sulfate, sulfonate, sulfamoyl, sulfonamido, sulfonyl, O, cyano, hydroxyl, unsubstituted alkoxy, substituted alkoxy, unsubstituted amino, substituted amino, unsubstituted amido, substituted amido, unsubstituted dialkyl amine, substituted dialkyl amine, unsubstituted heteroaryl, substituted heteroaryl, unsubstituted alkylthio, substituted alkylthio, unsubstituted carboxyl, substituted carboxyl, unsubstituted ester, or substituted ester.

In some forms, $X^8$ can be O.

In some forms, $R^{52}$ and $R^{53}$ can be independently hydrogen, unsubstituted alkyl, substituted alkyl, unsubstituted aryl, or substituted aryl.

In some forms, $R^{26}$-$R^{29}$ and $R^{31}$-$R^{32}$ can be independently hydrogen, halogen, sulfate, sulfonate, sulfonyl, unsubstituted alkyl, or substituted alkyl. Preferably, $R^{26}$-$R^{29}$ and $R^{31}$-$R^{32}$ can be independently hydrogen, H, Cl, Br, I, $SO_3H$, or unsubstituted alkyl.

In some forms, $R^{30}$ can be O, unsubstituted amino, substituted amino, substituted dialkyl amine, or unsubstituted dialkyl amine. Preferably, $R^{30}$ can be O, $NH_2$, or unsubstituted dialkylamine.

In some forms, $R^{32}$ can be hydrogen, unsubstituted alkoxy, substituted alkoxy, unsubstituted carboxyl, substituted carboxyl, unsubstituted ester, substituted ester, unsubstituted alkyl, substituted alkyl, unsubstituted amido, substituted amido, sulfate, or sulfonate. Preferably, $R^{32}$ can be hydrogen, $OR^{54}$, COOH, $COOR^{54}$, unsubstituted alkyl, $C(O)N(R^{54}R^{55})$, $NR^{54}C(O)R^{55}$, $SO_3H$, wherein $R^{54}$ and $R^{55}$ are independently hydrogen, unsubstituted alkyl, substituted alkyl, unsubstituted aryl, or unsubstituted aryl.

In some forms, $R^{33}$-$R^{37}$ can be independently hydrogen, halogen, unsubstituted alkoxy, substituted alkoxy, unsubstituted carboxyl, substituted carboxyl, unsubstituted ester, substituted ester, unsubstituted alkyl, substituted alkyl, unsubstituted amido, substituted amido, sulfate, or sulfonate. In some forms, $R^{33}$-$R^{37}$ can be independently hydrogen, F, Cl, Br, I, $OR^{54}$, COOH, $COOR^{54}$, unsubstituted alkyl, $C(O)N(R^{54}R^{55})$, $NR^{54}C(O)R^{55}$, or $SO_3H$, wherein $R^{54}$ and $R^{55}$ can be independently hydrogen, unsubstituted alkyl, substituted alkyl, unsubstituted aryl, or unsubstituted aryl.

In some forms, $R^{38}$ can be

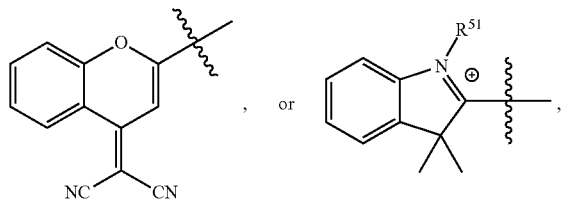

wherein $R^{51}$ can be unsubstituted alkyl, or substituted alkyl.

In some forms, $R^{39}$-$R^{43}$ can be independently hydrogen, halogen, unsubstituted alkoxy, substituted alkoxy, unsubstituted carboxyl, substituted carboxyl, unsubstituted ester, substituted ester, unsubstituted alkyl, substituted alkyl, unsubstituted aryl, substituted aryl, unsubstituted polyheteroaryl, substituted polyheteroaryl, unsubstituted amido, substituted amido, sulfate, or sulfonate. Preferably, $R^{39}$-$R^{43}$ can be independently hydrogen, F, Cl, Br, I, $OR^{54}$, COOH, $COOR^{54}$, unsubstituted alkyl, $C(O)N(R^{54}R^{55})$, $NR^{54}C(O)R^{55}$, $SO_3H$, or

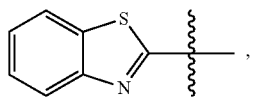

wherein $R^{54}$ and $R^{55}$ can be independently hydrogen, unsubstituted alkyl, substituted alkyl, unsubstituted aryl, or unsubstituted aryl.

In some forms, $R^{44}$ can be hydrogen, halogen, unsubstituted alkoxy, substituted alkoxy, unsubstituted carboxyl, substituted carboxyl, unsubstituted ester, substituted ester, unsubstituted alkyl, substituted alkyl, unsubstituted amido, substituted amido, sulfate, or sulfonate. Preferably, $R^{44}$ can be hydrogen, F, Cl, Br, I, $OR^{54}$, COOH, $COOR^{54}$, unsubstituted alkyl, $C(O)N(R^{54}R^{55})$, $NR^{54}C(O)R^{55}$, or $SO_3H$, wherein $R^{54}$ and $R^{55}$ are independently hydrogen, unsubstituted alkyl, substituted alkyl, unsubstituted aryl, or unsubstituted aryl.

In some forms, $R^{45}$-$R^{48}$ can be independently hydrogen, halogen, unsubstituted alkyl, substituted alkyl, sulfate, or sulfonate. Preferably, $R^{45}$-$R^{48}$ can be independently hydrogen, F, Cl, Br, I, $SO_3H$, unsubstituted alkyl, or substituted alkyl.

In some forms, $R^{49}$-$R^{50}$ can be independently hydrogen, halogen, unsubstituted alkoxy, substituted alkoxy, unsubstituted carboxyl, substituted carboxyl, unsubstituted ester, substituted ester, unsubstituted alkyl, substituted alkyl, unsubstituted amido, substituted amido, sulfate, or sulfonate. Preferably, $R^{49}$-$R^{50}$ can be independently hydrogen, F, Cl, Br, I, $OR^{54}$, COOH, $COOR^{54}$, unsubstituted alkyl, $C(O)N(R^{54}R^{55})$, $NR^{54}C(O)R^{55}$, or $SO_3H$, wherein $R^{54}$ and $R^{55}$ are independently hydrogen, unsubstituted alkyl, substituted alkyl, unsubstituted aryl, or unsubstituted aryl.

The metallic complexes described herein, preferably do not release the diagnostic, therapeutic, and/or prophylactic agent in the presence of oxygen, or in reducing conditions, such as the presence of glutathione in a cell. Preferably, the release of these agents is triggered by the presence of ascorbate, but not free metal ion or a reducing agent such as glutathione. The ascorbate-selective triggered-release of a diagnostic, therapeutic, and/or prophylactic agent can also include materials that can be activated by a stimulus such as ascorbate, i.e., stimulus responsive materials.

Every compound within the above definition is intended to be and should be considered to be specifically disclosed herein. Further, every subgroup that can be identified within the above definition is intended to be and should be considered to be specifically disclosed herein. As a result, it is specifically contemplated that any compound or subgroup of compounds can be either specifically included for or excluded from use or included in or excluded from a list of compounds. For example, any one or more of the compounds described herein, with a structure depicted herein, or referred to in the Examples herein can be specifically included, excluded, or combined in any combination, in a set or subgroup of such compounds. Such specific sets, subgroups, inclusions, and exclusions can be applied to any aspect of the compositions and methods described here. For example, a set of compounds that specifically excludes one or more particular compounds can be used or applied in the context of compounds per se (for example, a list or set of compounds), compositions including the compound (including, for example, pharmaceutical compositions), any one or more of the disclosed methods, or combinations of these. Different sets and subgroups of compounds with such specific inclusions and exclusions can be used or applied in the context of compounds per se, compositions including one or more of the compounds, or any of the disclosed methods. All of these different sets and subgroups of compounds—and the different sets of compounds, compositions, and methods using or applying the compounds—are specifically and individual contemplated and should be considered as specifically and individually described. As an example, the ligand-diagnostic agents #9

( 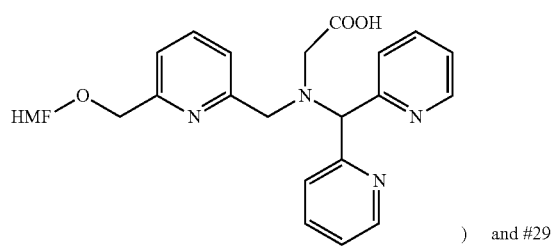 ) and #29

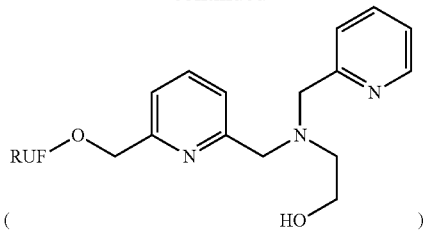

can be specifically included or excluded, as a group or individually, from any compounds per se (for example, a list or set of compounds), compositions including the compound (including, for example, pharmaceutical compositions), or any one or more of the disclosed methods, or combinations of these.

III. Formulations

The metal complexes described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients. See, e.g., *Remington's Pharmaceutical Sciences*, latest edition, by E. W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

These compositions can take the form of solutions, suspensions, emulsion, tablets, pills, capsules, powders, sustained-release formulations and the like.

A. Parenteral Formulations

The compounds described herein can be formulated for parenteral administration.

For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

If for intravenous administration, the compositions are packaged in solutions of sterile isotonic aqueous buffer. Where necessary, the composition may also include a solubilizing agent. The components of the composition are supplied either separately or mixed together in unit dosage form, for example, as a dry lyophilized powder or concentrated solution in a hermetically sealed container such as an ampoule or sachet indicating the amount of active agent. If the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to injection.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene, and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine, and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

1. Controlled Release Formulations

The parenteral formulations described herein can be formulated for controlled release including immediate release, delayed release, extended release, pulsatile release, and combinations thereof.

(a) Nano- and Microparticles

For parenteral administration, the one or more compounds, and optional one or more additional active agents, can be incorporated into microparticles, nanoparticles, or combinations thereof that provide controlled release of the compounds and/or one or more additional active agents. In forms wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, can also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents can be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

(b) Method of Making Nano- and Microparticles

Encapsulation or incorporation of drug into carrier materials to produce drug-containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some forms, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some forms, drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

2. Injectable/Implantable Formulations

The compounds described herein can be incorporated into injectable/implantable solid or semi-solid implants, such as polymeric implants. In some forms, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication requires polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

B. Enteral Formulations

Oral formulations can include standard carriers such as pharmaceutical grades of mannitol, lactose, sodium saccharine, starch, magnesium stearate, cellulose, magnesium carbonate, etc. Such compositions will contain a therapeutically effective amount of the compound and/or antibiotic together with a suitable amount of carrier so as to provide the proper form to the patient based on the mode of administration to be used.

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

1. Controlled Release Enteral Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another form, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another form, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

(a) Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred forms, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred forms, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred form, the acrylic polymer is an acrylic resin lacquer such as that which is commercially available from Rohm Pharma under the tradename EUDRAGIT®. In further preferred forms, the acrylic polymer comprises a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT® RL, 50% EUDRAGIT® RL and 50% EUDRAGIT t® RS, and 10% EUDRAGIT® RL and 90% EUDRAGIT® RS. One skilled in the art will recognize that other acrylic polymers may also be used, such as, for example, EUDRAGIT® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

(b) Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

IV. Methods of Making

The complexes can be synthesized using methods known in the art of metal complex synthesis such as methods that use free metals, metal salts, or other metal complexes precursors in a suitable solvent medium.

The ligands can be synthesized and conjugated to the diagnostic, therapeutic, or prophylactic agent as described in the examples below. In some forms, the diagnostic, therapeutic, or prophylactic agent is conjugated to a starting material from which the ligand is synthesized, prior to the synthesis of the ligand. In some forms the diagnostic, therapeutic, or prophylactic agent is conjugated to the ligand after the ligand has chelated the metal atom in the complex. Preferably, the diagnostic, therapeutic, or prophylactic agent is conjugated to the ligand after the ligand has been synthesized, but prior to formation of the metal complex.

Preferably, the metal complexes are synthesized starting from another metal salt such as $CuCl_2$, $Cu(OAc)_2$, and $Cu(OCl_4)_2$. One equivalent of the ligand containing the therapeutic, diagnostic, and/or prophylactic agent in DMSO is mixed with one equivalent the metal ion in a metal salt in water to generate the metal complexes. For example, 10 μL of 50 μM AP1 can be dissolved in DMSO and mixed thoroughly with 50 μM $Cu^{2+}$ in deionized water to generate the pAP1 complex. The complex can then be used as a probe.

V. Methods of Using

In some forms, the metal complexes can be used to detect the presence of ascorbate in a live biological sample, in a commercial sample, such as orange juice, or both. A bond cleavage, such as an ether bond cleavage, is triggered when ascorbate is present, leading to the release of a diagnostic agent, in which an emission can be measured after light excitation. In some forms, the method can be used to perform a quantitative measurement of ascorbate content a sample (live biological sample, commercial sample, or both).

In some forms, the metal complexes can be used to determine changes in amount of ascorbate over time such as in cellular environment in which ascorbate concentration can be altered as a result of administration of drugs, specific ascorbate transport inhibitors or stimulants which increase or deplete ascorbate content in cells.

Figure 6:
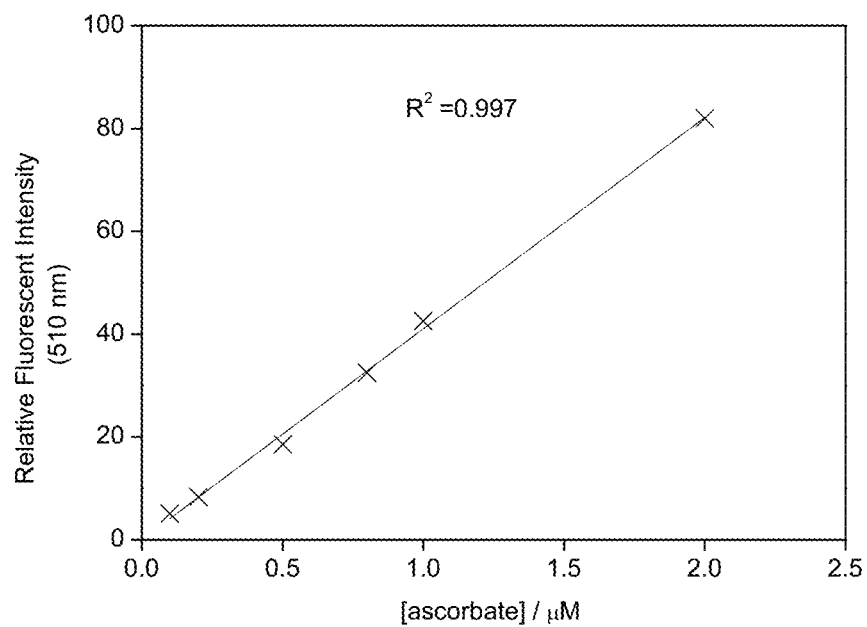
FIG. 6 shows relative fluorescent intensity of pAP1 against various concentrations of ascorbate.

In some forms, the probe is pAP1 with a fluorescein fluorophore. The fluorescent response of pAP1 can be selective only to ascorbate. As a non-limiting example, pAP1 was used to quantify the ascorbate content in a commercial fruit drink sample, such as YOU•C1000 vitamin Lemon. FIG. 6 shows the relative fluorescence intensity of the probe as a function of concentration of ascorbate in the sample. The linear curve shows that the probe's fluorescent response is proportional to the concentration of ascorbic acid in a sample. In FIG. 7, a spike-and-recovery experiment was performed. In the experiment, known amounts of ascorbic acid was spiked into the YOU•C1000 vitamin Lemon commercial drink. The fluorescence measurement showed a close to 100% recovery, demonstrating that the diluent or matrix does not inhibit or interfere with the probe. "Recovery" is an art-recognized term that refers to the fraction of an analyte determined after addition of a known amount the analyte to a sample.

Further, the probes can be used for optical imaging in live cells. Live cells treated with the probes in the presence or absence of ascorbic acid can be monitored using analytical tools, such as confocal microscopy. In some aspects, cells treated with the probes in the presence of ascorbic acid displayed enhanced fluorescence, compared to cells treated with probe in the absence of ascorbic acid. These show that the metal complexes can be used with the complex cellular matrix and that they will be useful for studying ascorbate biology in live biological samples. Although some fluorescence was observed in the cells not treated with ascorbic acid, this was background fluorescence. In addition, the metallic complexes can be used as a diagnostic tool for ascorbate-related diseases. Moreover, the ascorbate-cleavable part can also be coupled to other responsive units for the construction of other ascorbate-responsive materials. A particular property of the material can be triggered on/off by addition of ascorbate. A non-limiting example, is targeted drug release which could be triggered by ascorbate at a specific site.

The methods, compounds, and compositions herein described are further illustrated in the following examples, which are provided by way of illustration and are not intended to be limiting. It will be appreciated that variations in proportions and alternatives in elements of the components shown will be apparent to those skilled in the art and are within the scope of disclosed forms. Theoretical aspects are presented with the understanding that Applicants do not seek to be bound by the theory presented. All parts or amounts, unless otherwise specified, are by weight.

EXAMPLES

Example 1: Synthesis of Fluorescein Containing Probe AP1 (Ligand-Fluorophore Conjugate)

Materials and Methods

All solvents were of reagent grade. All commercially purchased chemicals were used as received. Ascorbic acid was purchased from Sigma-Aldrich. 2-picolylamine and benzaldehyde were purchased from AK science. 2,6-dichloromethylpyridine was synthesized according to the literature. Fluorescein derivative 1c was synthesized according to methods known in the art.

A schematic for the synthesis of AP1 ligand is shown in scheme 1 below. Scheme 1:

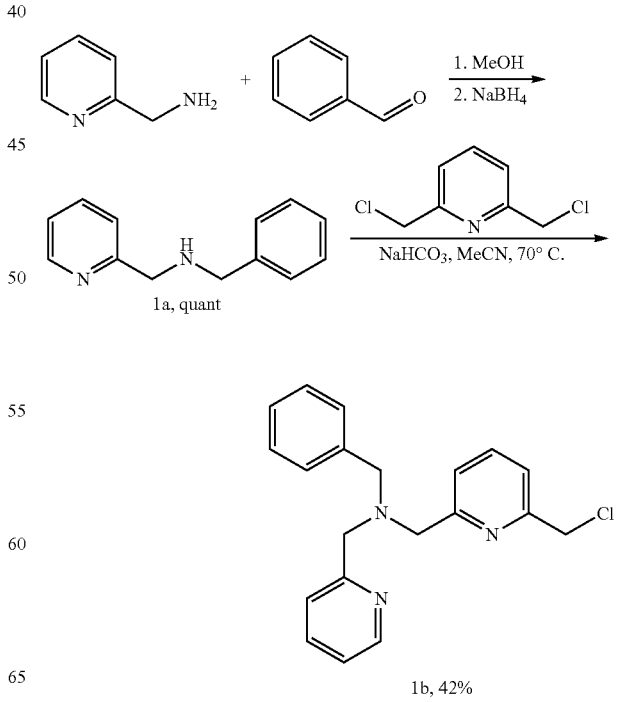

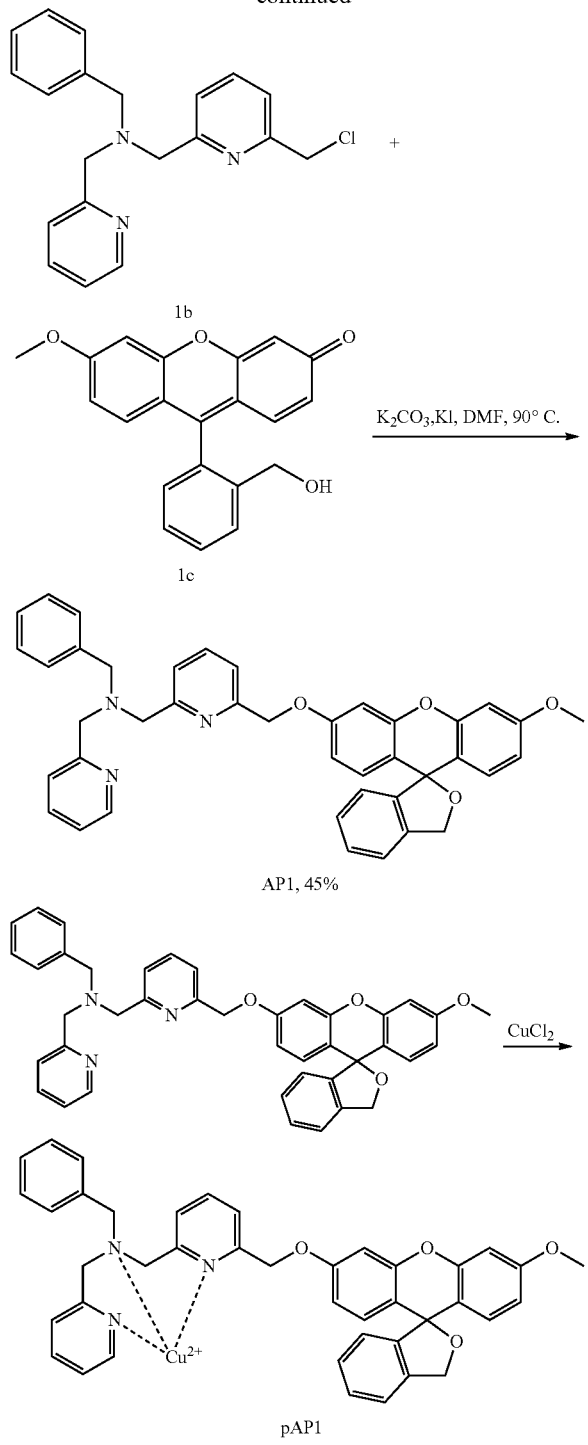

evaporator to give benzyl-pyridin-2-ylmethyl-amine (1a) which was used in the next step without further purification. Yield=0.79 g, quant.

(ii) Synthesis of 1b

A mixture of 2,6-dichloromethylpyridine (1.4 g, 8.0 mmol) and $NaHCO_3$ (0.17 g, 2.0 mmol) in 40 ml MeCN was heated at 70° C. A solution of benzyl-pyridin-2-ylmethyl-amine 1a (0.40 g, 2.0 mmol, 25 ml) in the same solvent was slowly added. The resulting mixture was stirred at 70° C. overnight and cooled to room temperature. Insoluble materials were removed by filtration. The filtrate was concentrated and purified by a basic alumina column (1:4 ethyl acetate/hexane). The product was obtained as pale yellow oil. Yield=0.28 g, 42%.

(iii) Synthesis of Ligand of Ascorbate Probe Ligand (AP1)

A mixture of fluorescein derivative 1c (0.1 g, 0.30 mmol) and compound 1b (0.10 g, 0.30 mmol), $K_2CO_3$ (0.21 g, 1.5 mmol) and KI (50 mg, 0.30 mmol) in 40 ml DMF was heated at 90° C. overnight. After cooling to room temperature, insoluble materials were removed by filtration, and the filtrate was purified by a basic alumina column (100% ethyl acetate). The product was isolated as a pale yellow solid. Yield=86 mg, 45%.

(iv) Generating the Ascorbate Probe (pAP1)

Ascorbate probe ligand (AP1) was dissolved in ethyl acetate to generate a 5 mM solution. The 5-mM ascorbate probe ligand solution was aliquoted into 200 μL PCR tubes, dried completely in a desiccator in vacuum for 24 hours and stored at −20° C. Ascorbate probe ligand can be regenerated by adding DMSO into the PCR tube. 10 μL of 5 mM AP1 probe ligand in DMSO was mixed with 10 μL of 5 mM $CuCl_2$ in water. The solution was mixed thoroughly for 10-30 mins for complexation.

(v) Fluorescence Measurement

Unless otherwise specified, the sample was excited at $\lambda_{ex}$=470 nm and the emission intensity at $\lambda_{em}$=510 nm was taken as the fluorescence intensity of Ascorbate probe (pAP1).

Figure 2A:
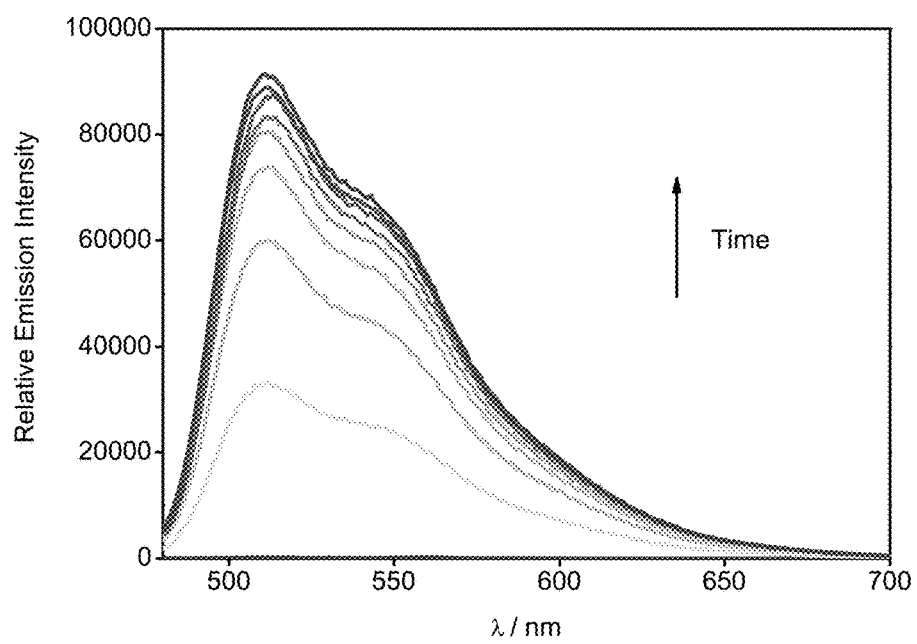
FIGS. 2A-2H show fluorescence data for investigations using pAP1.
Figure 2B:
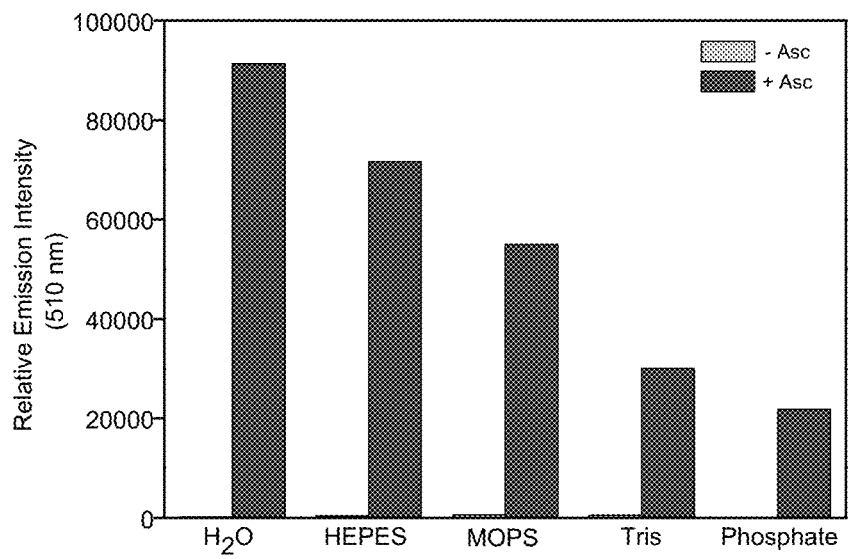
Figure 2C:
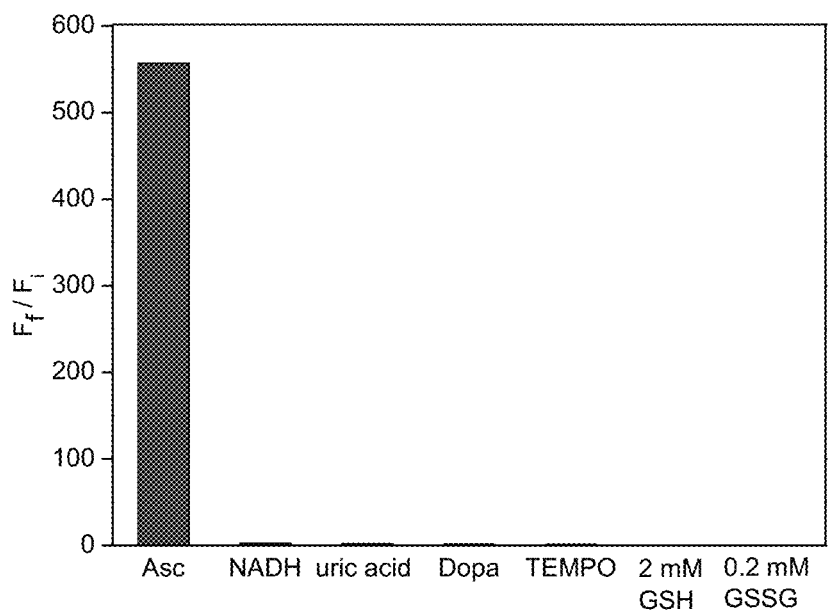
Figure 2D:
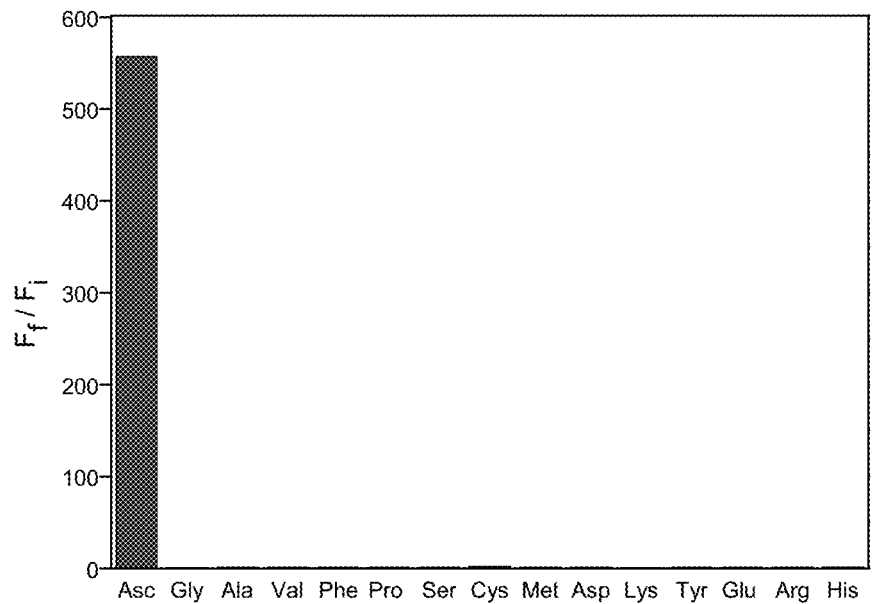
Figure 2E:
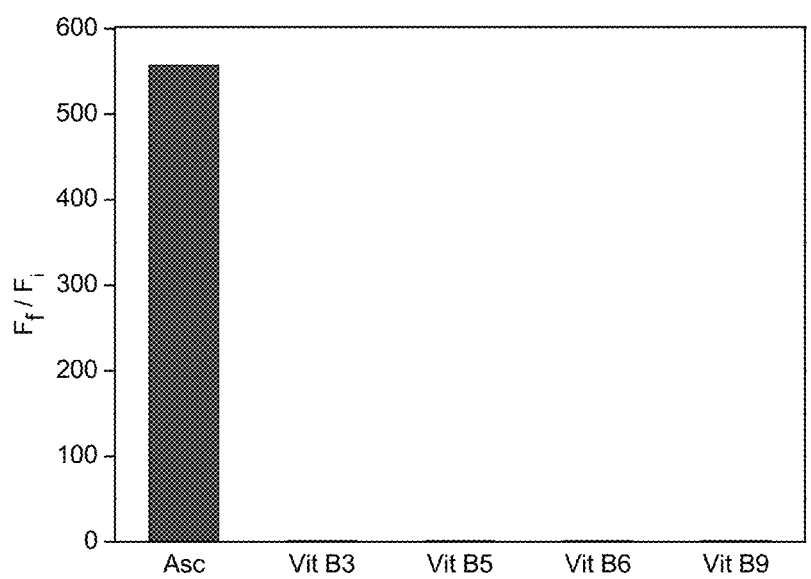
Figure 2F:
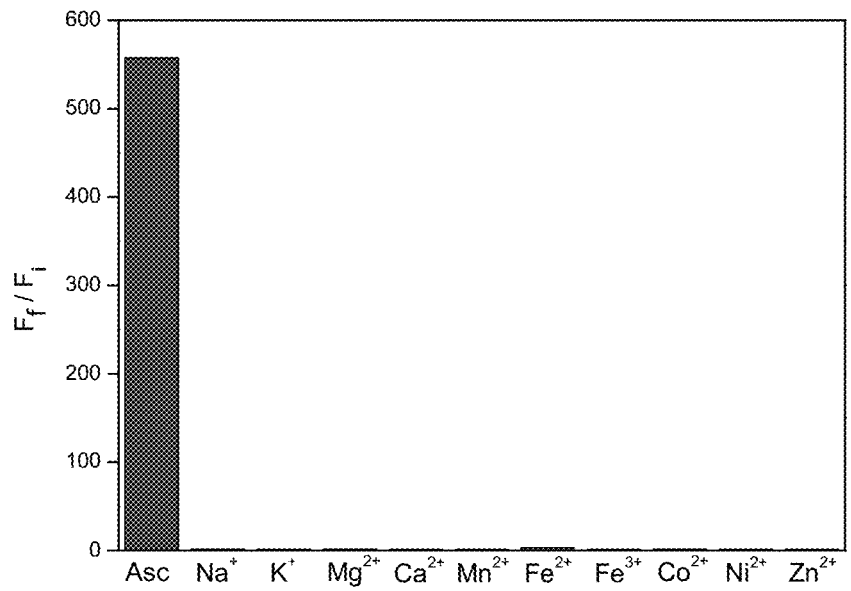
Figure 2G:
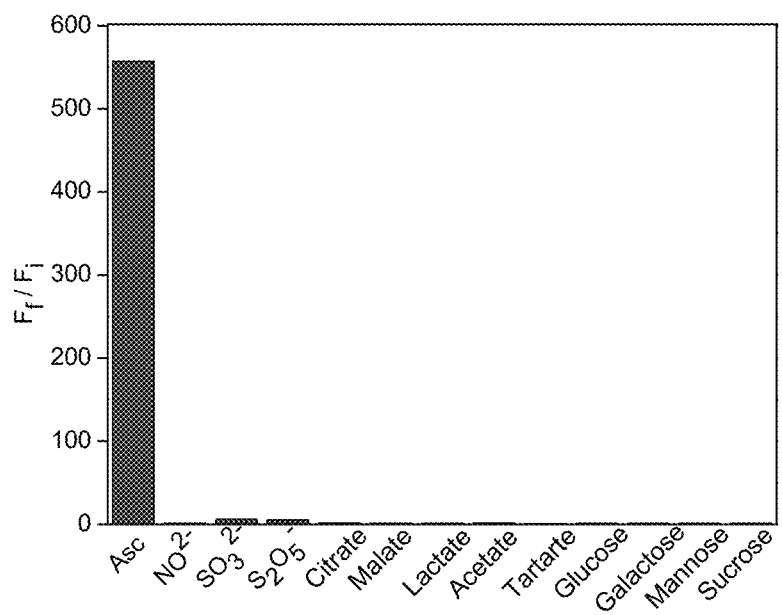
Figure 2H:
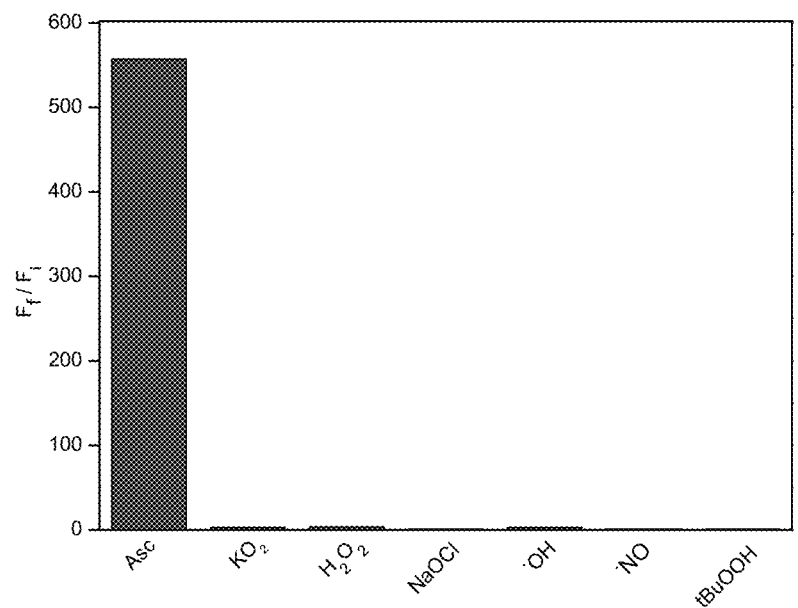

2 μL of the pAP1 complex solution was pipetted into 996 μL of deionized water or buffers in a 1.5-mL Y-shaped quartz cuvette. The solution was mixed thoroughly by pipetting and allowed to stand for 15-30 mins. After this time, a fluorescence measurement was taken and this value was used as the fluorescence intensity at 0 min. 2 μL of ascorbic acid in deionized water was added subsequently and was allowed to stand for 30 mins, and another fluorescence measurement was taken. The final concentration of pAP1 and ascorbic acid solutions were 5 μM and 100 μM, respectively. FIG. 2A shows the kinetics acquired by taking the fluorescence spectrum at 0, 2, 4, 6, 8, 10, 15, 20, 30 min, after the addition of 50 mM of ascorbic acid solution. FIG. 2B shows fluorescence intensities measured in various buffers (pH 7.4, 50 mM) FIGS. 2C to 2H show the fluorescence ratio that was calculated by dividing the fluorescence intensity at 30 mins by the fluorescence intensity at 0 mins. The analytes were added to achieve a 100 μM concentration.

Example 2: Synthesis of Resorufin Containing Probe AP2 (Ligand-Fluorophore Conjugate)

Materials and Methods

All solvents were of reagent grade. All commercially purchased chemicals were used as received. Ascorbic acid was purchased from Sigma-Aldrich. 2-picolylamine and benzaldehyde were purchased from AK science. 2,6-dichlo- (i) Synthesis of 1a A mixture of 2-picolylamine (0.41 ml, 4.0 mmol) and benzaldehyde (0.4 ml, 4.0 mmol) in 40 ml MeOH was stirred at room temperature for 2 hours. The solution was cooled in an ice bath, $NaBH_4$ (0.3 g, 8 mmol) was added in small portions. The mixture was slowly warmed to room temperature, and stirred for 1 hour. Solvent was removed and the residue was re-dissolved in $CH_2Cl_2$, washed with saturated $K_2CO_3$ solution twice and with a solution of brine and dried over $MgSO_4$. Solvents were removed by a rotatory romethylpyridine was synthesized according to methods known in the art. Resorufin sodium salt was obtained from Sigma-Aldrich.

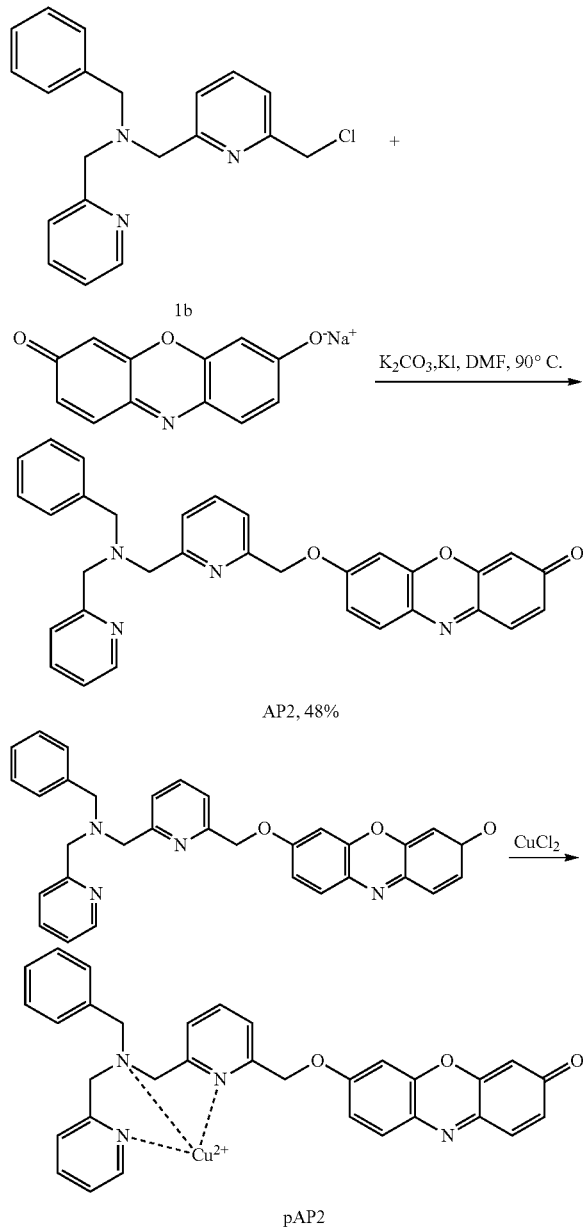

A mixture of resorufin sodium salt (0.12 g, 0.50 mmol), compound 1b (0.17 g, 0.50 mmol), $K_2CO_3$ (0.35 g, 2.5 mmol) and KI (83 mg, 0.50 mmol) in 40 ml DMF was heated at 90° C. overnight. After cooling to room temperature, insoluble materials were removed by filtration; the filtrate was concentrated and purified by a basic alumina column (100% ethyl acetate→50:1 ethyl acetate/MeOH). The product was isolated as a dark red solid. Yield=0.12 g, 48%.

(i) Generating the Ascorbate Probe (pAP2)

Ascorbate probe ligand (AP2) was dissolved in ethyl acetate to generate a 5-mM solution. The 5 mM ascorbate probe ligand solution was aliquoted into 200 μL PCR tubes, dried completely in a desiccator in vacuum for 24 hours and stored at −20° C. Ascorbate probe ligand can be regenerated by adding DMSO into the PCR tube. 10 μL of 5 mM AP2 probe ligand in DMSO was mixed with 10 μL of 5 mM $CuCl_2$ in water. The solution was mixed thoroughly for 10-30 mins for complexation.

(ii) Fluorescence Measurement

The sample was excited at $\lambda_{ex}$=570 nm and the emission intensity at $\lambda_{em}$=585 nm was taken as the fluorescence intensity of ascorbate probe (pAP2).

Figure 3A:
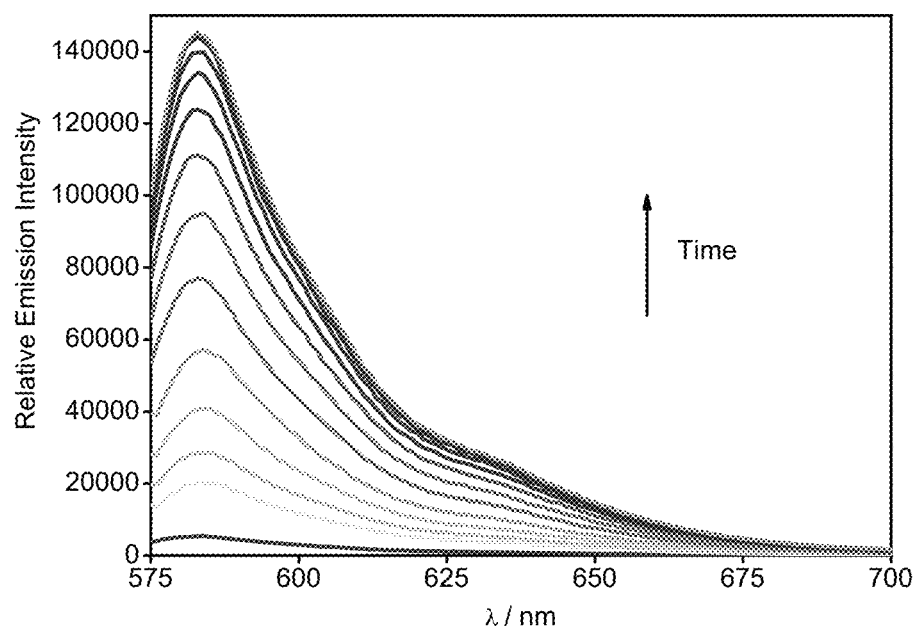
FIG. 3A shows a fluorescence response of 5 μM of a probe containing AP2 (pAP2) upon reaction of 20 eq Asc for 30 mins ($\lambda_{ex}$=570 nm). Spectra were acquired in deionized water.
Figure 3B:
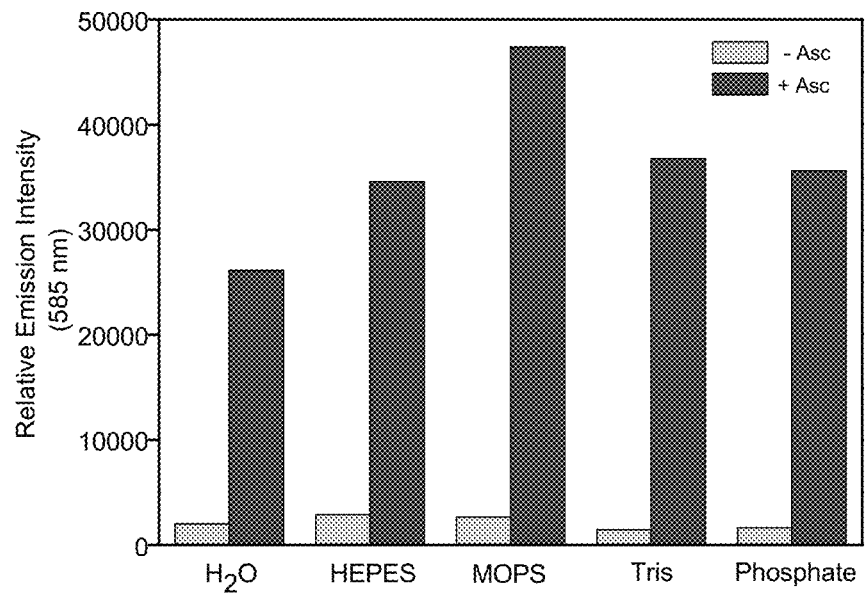
FIG. 3B shows a fluorescence response of a 5-μM solution of pAP2 upon reaction of 20 eq Asc with $\lambda_{ex}$=570 nm in various buffers (pH 7.4, 50 mM).

2 μL of the pAP2 complex solution was pipetted into 996 μL of deionized water or buffers in a 1.5-mL Y-shaped quartz cuvette. The solution was mixed thoroughly by pipetting and was allowed to stand for 15-30 mins. After this time, a fluorescence measurement was taken and this value used as the fluorescence intensity at 0 min. 2 μL of ascorbic acid in deionized water was added subsequently and was allowed to stand for 30 mins, and another fluorescence measurement was taken. The final concentration of pAP2 and ascorbic acid solution were 5 μM and 100 μM, respectively. FIG. 3A shows the kinetics acquired by taking the fluorescence spectrum at 0, 2, 4, 6, 8, 10, 15, 20, 30 min, after the addition of 50 mM of ascorbic acid solution. FIG. 3B shows fluorescence intensities measured in various buffers (pH 7.4, 50 mM).

Example 3: Synthesis of Coumarin Containing Probe AP3 (Ligand-Fluorophore Conjugate)

Materials and Methods

All solvents were of reagent grade. All commercially purchased chemicals were used as received. Ascorbic acid was purchased from Sigma-Aldrich. 2-picolylamine and benzaldehyde were purchased from AK science. 2,6-dichloromethylpyridine was synthesized according to methods known in the art. 7-hydroxycoumarin was obtained from J&K Scientific.

A schematic for the synthesis of the AP3 ligand is shown in Scheme 2 below. Scheme 2.

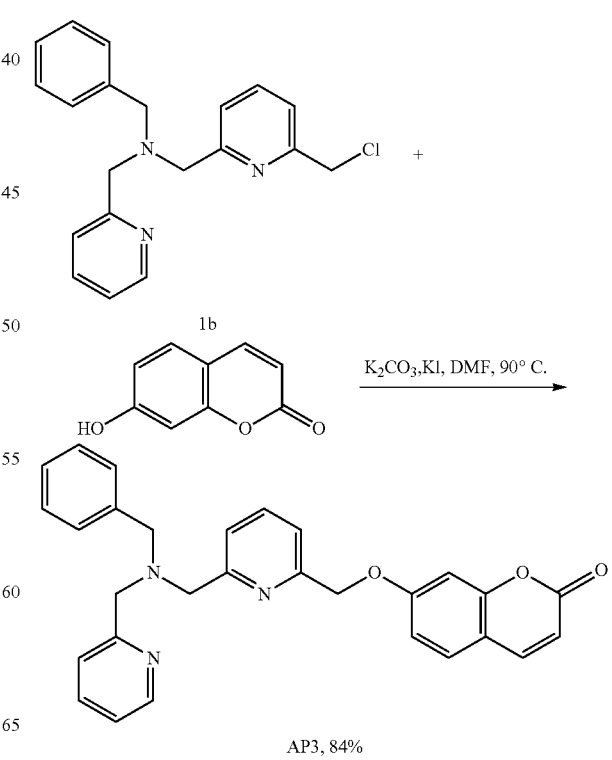

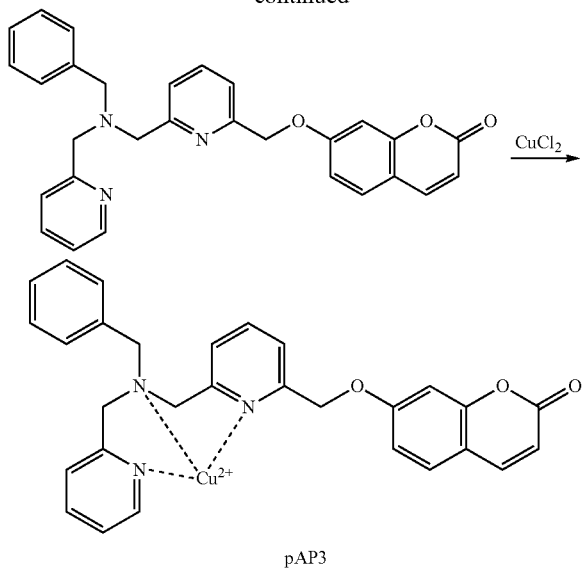

pAP3

A mixture of umbelliferone (85 mg, 0.53 mmol), compound 1b (0.18 g, 0.53 mmol), $K_2CO_3$ (0.37 g, 2.7 mmol) and KI (88 mg, 0.53 mmol) in 40 ml DMF was heated at 90° C. overnight. After cooling to room temperature, insoluble materials were removed by filtration, the filtrate was concentrated and purified by a basic alumina column (100% ethyl acetate). The product was isolated as a pale yellow solid. Yield=0.21 g, 84%.

Generating the Ascorbate Probe (pAP3)

Ascorbate probe ligand (AP3) was dissolved in ethyl acetate to generate a 5-mM solution. The 5-mM ascorbate probe ligand solution was aliquoted into 200 µL PCR tubes, dried completely in a desiccator in vacuum for 24 hours and stored at −20° C. Ascorbate probe ligand can be regenerated by adding DMSO into the PCR tube. 10 µL of 5 mM AP3 probe ligand in DMSO was mixed with 10 µL of 5 mM $CuCl_2$ in water. The solution was mixed thoroughly for 10-30 mins for complexation.

Fluorescence Measurement

The sample was excited at $\lambda_{ex}$=325 nm and the emission intensity at $\lambda_{em}$=455 nm was taken as the fluorescence intensity of Ascorbate probe (pAP1).

Figure 4A:
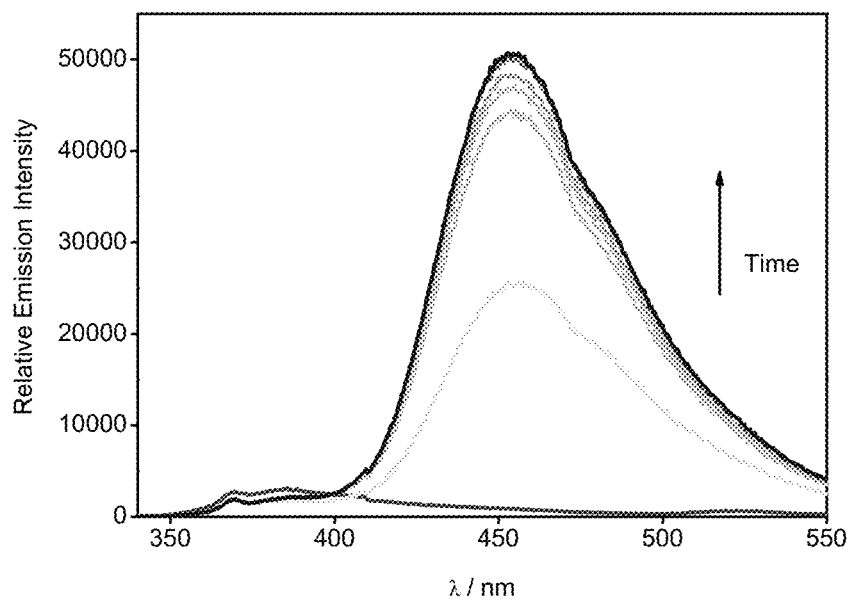
FIG. 4A shows a fluorescence response of 5 μM of a probe containing AP3 (pAP3) upon reaction of 20 eq Asc for 30 mins ($\lambda_{ex}$=325 nm). Spectra were acquired in deionized water.
Figure 4B:
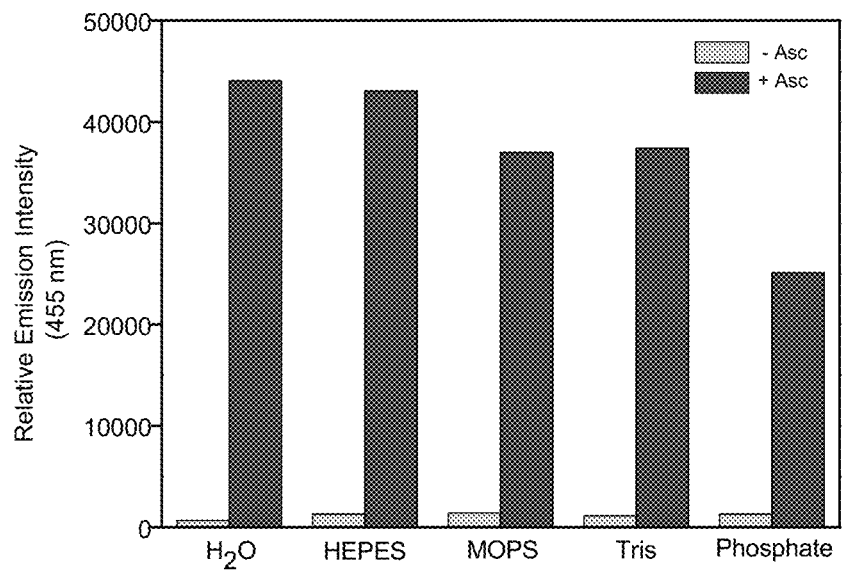
FIG. 4B shows a fluorescence response of a 5-μM solution of pAP3 upon reaction of 20 eq Asc with $\lambda_{ex}$=325 nm in various buffers (pH 7.4, 50 mM).

2 µL of the pAP3 complex solution was pipetted into 996 µL of deionized water or buffers in a 1.5-mL Y-shaped quartz cuvette. The solution was mixed thoroughly by pipetting and was allowed to stand for 15-30 mins. After this time, a fluorescence measurement was taken and this value was used as the fluorescence intensity 0 min. 2 µL of ascorbic acid in deionized water was added subsequently and allowed to stand for 30 mins, and another fluorescence measurement was taken. The final concentration of pAP3 and ascorbic acid solution were 5 µM and 100 µM, respectively. FIG. 4A shows the kinetics acquired by taking the fluorescence spectrum at 0, 1, 3, 5, 10, 20, 30 min, after the addition of 50 mM of ascorbic acid solution. FIG. 4B shows the fluorescence ratio (fluorescent intensity at 30 mins divided by fluorescence intensity at 0 mins) measured in various buffers (pH 7.4, 50 mM).

Example 4: Synthesis of 2-(2-Hydroxyphenyl)Benzothiazole (HBT) Containing Probe AP4 (Ligand-Fluorophore Conjugate)

Materials and Methods

All solvents were of reagent grade. All commercially purchased chemicals were used as received. Ascorbic acid was purchased from Sigma-Aldrich. 2-picolylamine and benzaldehyde were purchased from AK science. 2,6-dichloromethylpyridine and 2-(2-hydroxyphenyl)benzothiazole were synthesized according to methods known in the art.

A schematic for the synthesis of the AP4 ligand is shown in Scheme 3 below. Scheme 3.

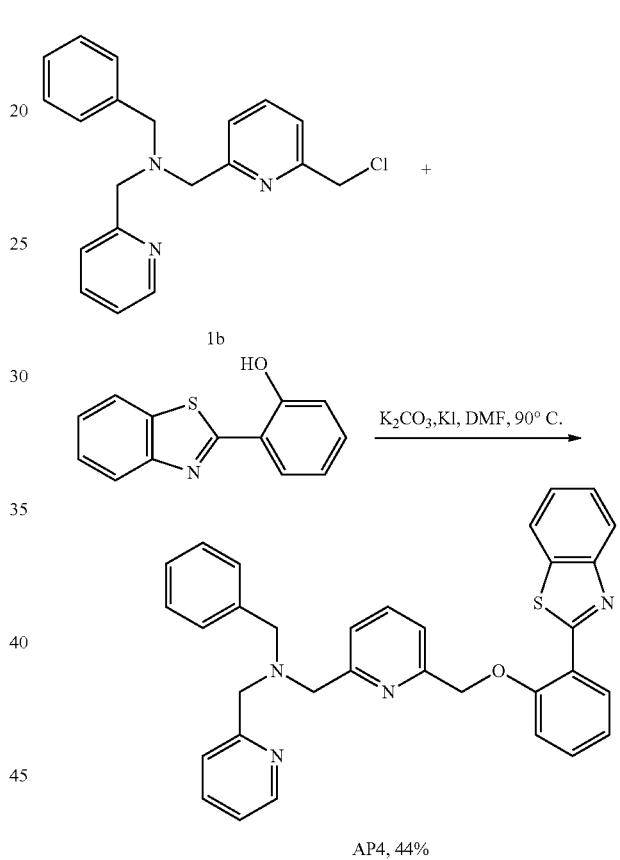

AP4, 44%

A mixture of 2-(2-hydroxyphenyl)benzothiazole (68 mg, 0.30 mmol), compound 1b (0.1 g, 0.30 mmol), $K_2CO_3$ (0.21 g, 1.5 mmol) and KI (50 mg, 0.30 mmol) in 40 ml DMF was heated at 90° C. overnight. After cooling to room temperature, insoluble materials were removed by filtration, and the filtrate was concentrated and purified by a basic alumina column (1:4 ethyl acetate/hexane→100% ethyl acetate). The product was isolated as a pale yellow solid. Yield=70 mg, 44%.

Generating the Ascorbate Probe (pAP4)

Ascorbate probe ligand (AP4) was dissolved in ethyl acetate to generate a 5-mM solution. The 5-mM ascorbate probe ligand solution was aliquoted into 200 µL PCR tubes, dried completely in a desiccator in vacuum for 24 hours and stored at −20° C. Ascorbate probe ligand can be regenerated by adding DMSO into the PCR tube. 10 µL of 5 mM AP4 probe ligand in DMSO was mixed with 10 µL of 5 mM CuCl$_2$ in water. The solution was mixed thoroughly for 10-30 mins for complexation.

Fluorescence Measurement

The sample was excited at $\lambda_{ex}$=325 nm and the emission intensity at $\lambda_{em}$=370, 455 nm was taken as the fluorescence intensity of Ascorbate probe (pAP1).

Figure 5A:
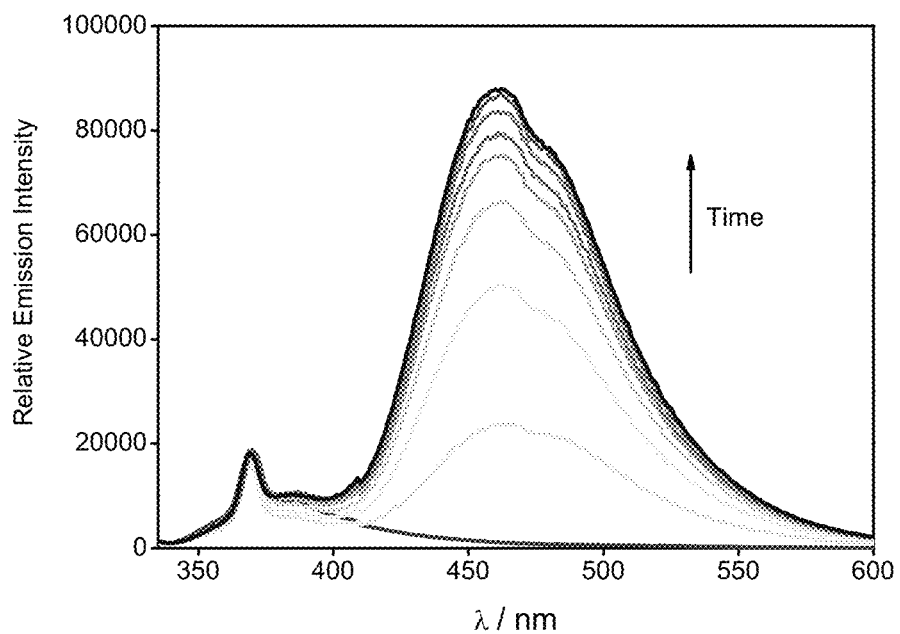
FIG. 5A shows a fluorescence response of 5 μM of a probe containing AP4 (pAP4) upon reaction of 20 eq Asc for 30 mins ($\lambda_{ex}$=325 nm). Spectra were acquired in deionized water.
Figure 5B:
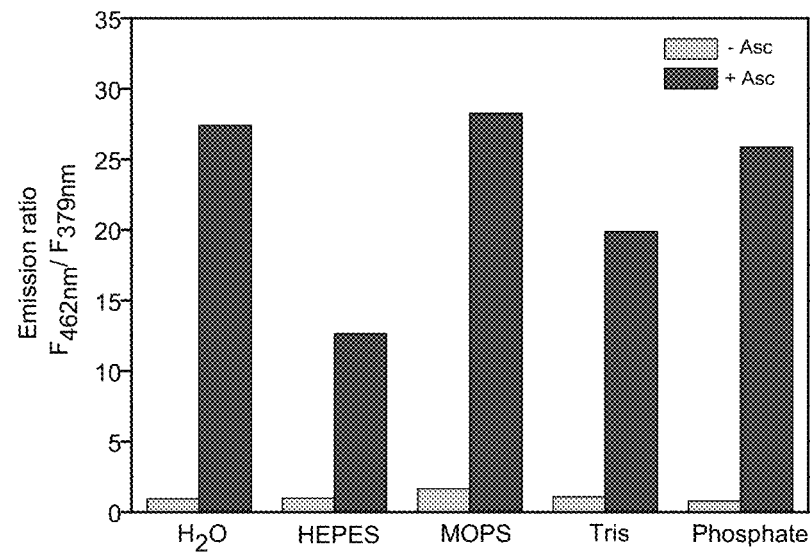
FIG. 5B shows a fluorescence response of a 5-μM solution of pAP4 upon reaction of 20 eq Asc with $\lambda_{ex}$=325 nm in various buffers (pH 7.4, 50 mM).

2 μL of the pAP4 complex solution was pipetted into 996 μL of deionized water or buffers in a 1.5-mL Y-shaped quartz cuvette. The solution was mixed thoroughly by pipetting and was allowed to stand for 15-30 mins. A fluorescence measurement was taken and this value was used as the fluorescence intensity at 0 min. 2 μL of ascorbic acid in deionized water was added subsequently and was allowed to stand for 30 mins, and another fluorescence measurement was taken. The final concentration of pAP4 and ascorbic acid solution were 5 μM and 100 μM, respectively. FIG. 5A shows the kinetics acquired by taking the fluorescence spectrum at 0, 2, 4, 6, 8, 10, 15, 20, 30 min, after the addition of 50 mM of ascorbic acid solution. FIG. 5B shows the emission ratio (fluorescence intensity ratio at 30 min of 455 nm and 370 nm divided by fluorescence intensity ratio at 0 min of 455 nm and 370 nm) measured in various buffers (pH 7.4, 50 mM).

Example 5: Synthesis of Resorufin Containing Probe APS1 (Ligand-Fluorophore Conjugate)

Materials and Methods

All solvents were of reagent grade. All commercially purchased chemicals were used as received. Ascorbic acid was purchased from Sigma-Aldrich. 2-(ethylthio)ethylamine and benzaldehyde were purchased from J&K Scientific and AK science. 2,6-dichloromethylpyridine was synthesized according to methods known in the art. Resorufin sodium salt was obtained from Sigma-Aldrich.

A schematic for the synthesis of the APS1 ligand is shown in Scheme 4 below. Scheme 4.

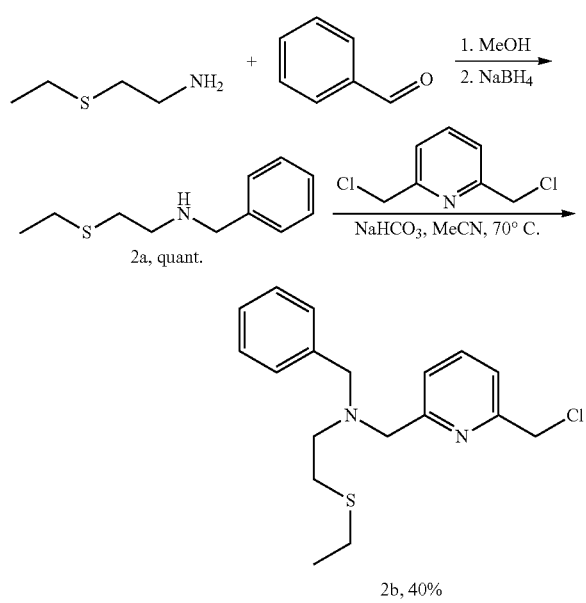

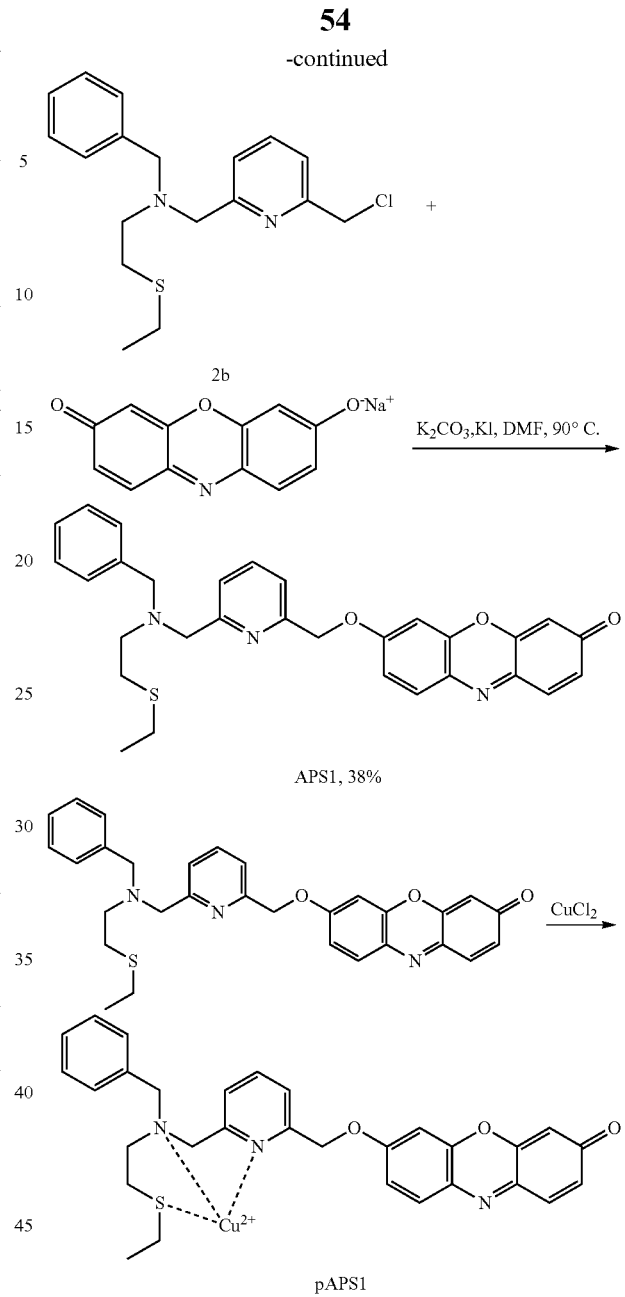

(i) Synthesis of 2a

A mixture of 2-(ethylthio)ethylamine (0.22 ml, 2.0 mmol) and benzaldehyde (0.20 ml, 2.0 mmol) in 40 ml MeOH was stirred at room temperature for 2 hours. The solution was cooled in an ice bath, NaBH$_4$ (0.15 g, 4.0 mmol) was added in small portions. The mixture was slowly warmed to room temperature and stirred for 1 hour. Solvents were removed and the residue was re-dissolved in CH$_2$Cl$_2$, washed with saturated K$_2$CO$_3$ solution twice and brine, and dried over MgSO$_4$. Solvents were removed by a rotatory evaporator to give crude 2a which was used in the next step without further purification. Yield=0.49 g, quant.

(ii) Synthesis of 2b

To a mixture of 2,6-dichloromethylpyridine (0.84 g, 4.8 mmol) and NaHCO$_3$ (0.10 g, 1.2 mmol) in 40 ml MeCN heated at 70° C., a solution of 2a (0.24 g, 1.2 mmol) in the same solvent was slowly added. The resulting mixture was stirred at 70° C. overnight and cooled to room temperature.

Insoluble materials were removed by filtration. The filtrate was concentrated and purified by a basic alumina column (1:5 ethyl acetate/hexane). The product was obtained as a pale yellow oil. Yield=0.16 g, 40%.

(iii) Synthesis of Ascorbate Probe Ligand (APS1)

A mixture of resorufin sodium salt (0.11 g, 0.48 mmol), compound 2b (0.16 g, 0.48 mmol), $K_2CO_3$ (0.33 g, 2.4 mmol) and KI (80 mg, 0.48 mmol) in 40 ml DMF was heated at 90° C. overnight. After cooling to room temperature, insoluble materials were removed by filtration, and the filtrate was concentrated and purified by a basic alumina column (100% ethyl acetate→50:1 ethyl acetate/MeOH). The product was isolated as a dark red solid. Yield=93 mg, 38%.

(iv) Generating the Ascorbate Probe (pAPS1)

Ascorbate probe ligand (APS1) was dissolved in ethyl acetate to generate a 5-mM solution. The 5-mM ascorbate probe ligand solution was aliquoted into 200 μL PCR tubes, dried completely in a desiccator in vacuum for 24 hours and stored at −20° C. Ascorbate probe ligand can be regenerated by adding DMSO into the PCR tube. 10 μL of 5 mM APS1 probe ligand in DMSO was mixed with 10 μL of 5 mM $CuCl_2$ in water. The solution was mixed thoroughly for 10-30 mins for complexation.

Example 6: Synthesis of Resorufin Containing Probe APS-2 (Ligand-Fluorophore Conjugate)

Materials and Methods

All solvents were of reagent grade. All commercially purchased chemicals were used as received. Ascorbic acid was purchased from Sigma-Aldrich. 2-(ethylthio)ethylamine and 2-pyridylcarboxyaldehyde were purchased from J&K Scientific and AK science. 2,6-dichloromethylpyridine was synthesized according to methods known in the art. Resorufin sodium salt was obtained from Sigma-Aldrich.

A schematic for the synthesis of the APS2 ligand is shown in Scheme 5 below. Scheme 5.

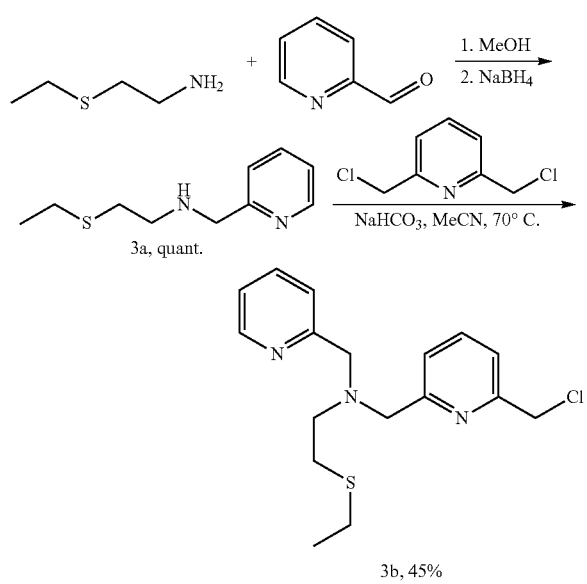

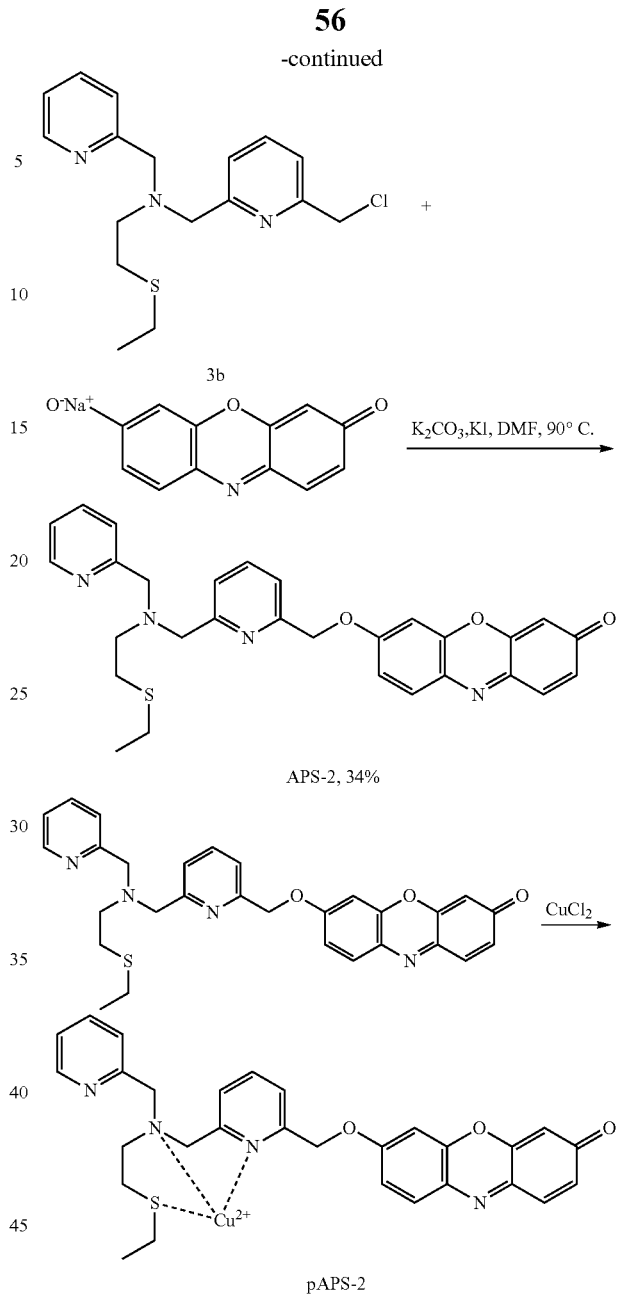

(i) Synthesis of 3a

A mixture of 2-(ethylthio)ethylamine (0.22 ml, 2.0 mmol) and 2-pyridylcarboxyaldehyde (0.19 ml, 2.0 mmol) in 40 ml MeOH was stirred at room temperature for 2 hours. The solution was cooled in an ice bath and $NaBH_4$ (0.15 g, 4 mmol) was added in small portions. The mixture was slowly warmed to room temperature and stirred for 1 hour. Solvents were removed and the residue re-dissolved in $CH_2Cl_2$, washed with saturated $K_2CO_3$ solution twice and brine, and dried over $MgSO_4$. Solvents were removed by a rotatory evaporator to give crude 3a which was used in the next step without further purification. Yield=0.52 g, quant.

(ii) Synthesis of 3b

To a mixture of 2,6-dichloromethylpyridine (2.8 g, 16 mmol) and $NaHCO_3$ (0.34 g, 4.0 mmol) in 60 ml MeCN heated at 70° C., a solution of 3a (0.79 g, 4.0 mmol) in the same solvent was slowly added. The resulting mixture was stirred at 70° C. overnight and cooled to room temperature.

Insoluble materials were removed by filtration. The filtrate was concentrated and purified by a basic alumina column (1:2 ethyl/hexane). The product was obtained as a pale yellow oil. Yield=0.61 g, 45%.

(iii) Synthesis of Ascorbate Probe Ligand (APS2)

A mixture of resorufin sodium salt (0.19 g, 0.80 mmol), compound 3b (0.27 g, 0.80 mmol), K₂CO₃ (0.61 g, 4.0 mmol) and KI (0.13 g, 0.80 mmol) was heated at 90° C. overnight. After cooling to room temperature, insoluble materials were removed by filtration, and the filtrate was concentrated and purified by a basic alumina column (100% ethyl acetate→50:1 ethyl acetate/MeOH). The product was isolated as a dark red solid. Yield=0.14 g, 34%.

(iv) Generating the Ascorbate Probe (pAPS2)

Ascorbate probe ligand (APS2) was dissolved in ethyl acetate to generate a 5-mM solution. The 5-mM ascorbate probe ligand solution was aliquoted into 200 µL PCR tubes, dried completely in a desiccator in vacuum for 24 hours and stored at −20° C. Ascorbate probe ligand can be regenerated by adding DMSO into the PCR tube. 10 µL of 5 mM AP21 probe ligand in DMSO was mixed with 10 µL of 5 mM CuCl₂ in water. Mixed thoroughly for 10-30 mins for complexation.

Example 7: Synthesis of Ascorbate Probe Containing AP1OMe (Ligand-Fluorophore Conjugate)

Materials and Methods

All solvents were of reagent grade. All commercially purchased chemicals were used as received. Ascorbic acid was purchased from Sigma-Aldrich. 2-pyridylcarboxyaldehyde were purchased from AK science. o-anisaldehyde and 2,6-dichloromethylpyridine were synthesized according to methods known in the art. Resorufin sodium salt was obtained from Sigma-Aldrich.

A schematic for the synthesis of the AP1OMe ligand is shown in Scheme 6 below.

Scheme 6.

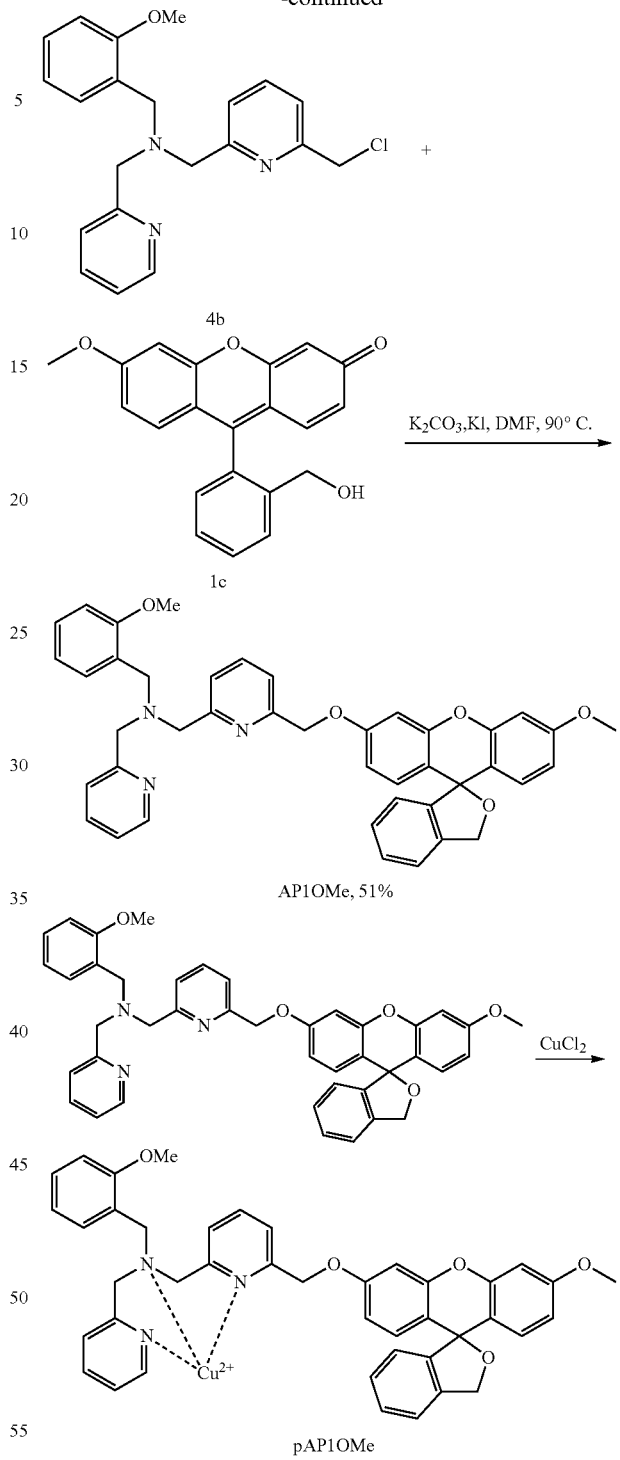

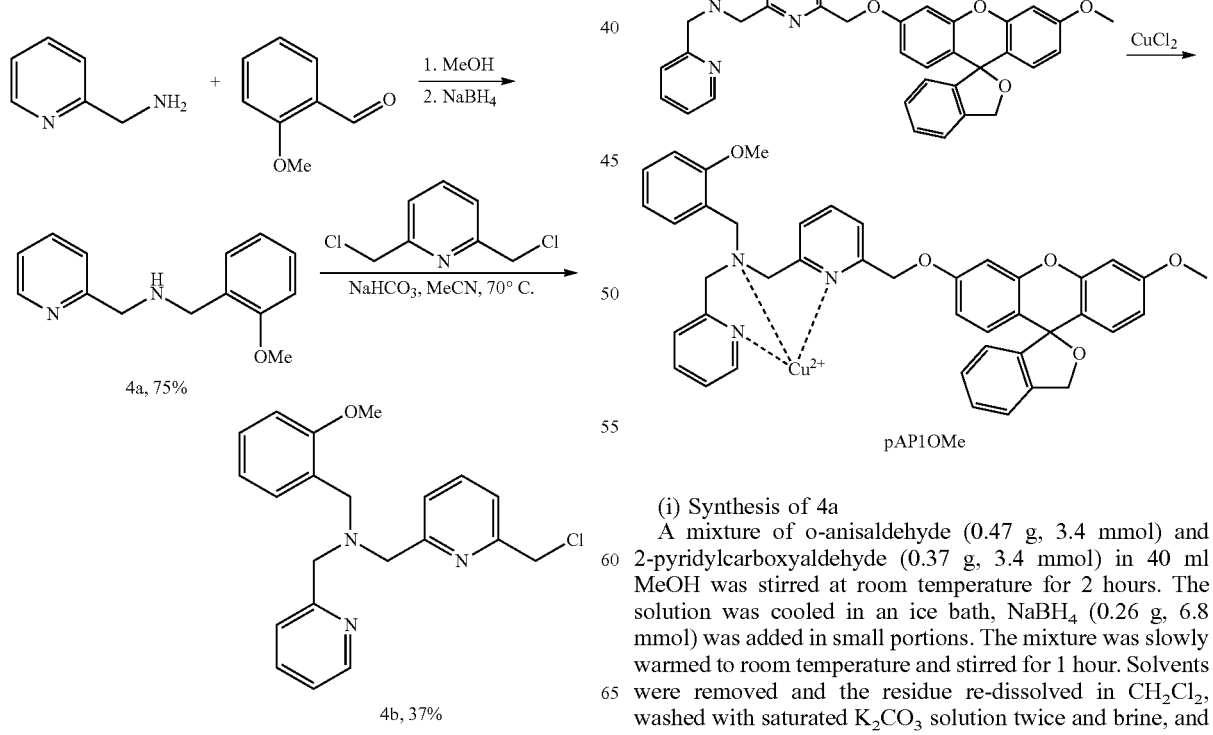

(i) Synthesis of 4a

A mixture of o-anisaldehyde (0.47 g, 3.4 mmol) and 2-pyridylcarboxyaldehyde (0.37 g, 3.4 mmol) in 40 ml MeOH was stirred at room temperature for 2 hours. The solution was cooled in an ice bath, NaBH₄ (0.26 g, 6.8 mmol) was added in small portions. The mixture was slowly warmed to room temperature and stirred for 1 hour. Solvents were removed and the residue re-dissolved in CH₂Cl₂, washed with saturated K₂CO₃ solution twice and brine, and dried over MgSO₄. Solvents were removed by a rotatory evaporator to give crude 4a which was used in the next step without further purification. Yield=0.58 g, 75%.

(ii) Synthesis of 4b

To a mixture of 2,6-dichloromethylpyridine (0.77 g, 0.44 mmol) and NaHCO$_3$ (92 mg, 0.11 mmol) in 60 ml of MeCN heated at 70° C., a solution of 4a (0.25 g, 0.11 mmol) in the same solvent was slowly added. The resulting mixture was stirred at 70° C. overnight and cooled to room temperature. Insoluble materials were removed by filtration. The filtrate was concentrated and purified by a basic alumina column (1:2 ethyl acetate/hexane). The product was obtained as a pale yellow oil. Yield=0.15 g, 37%.

(iii) Synthesis of Ascorbate Probe Ligand (AP1OMe)

A mixture of the fluorescein derivative 1c (0.11 g, 0.41 mmol), compound 4b (0.14 g, 0.41 mmol) K$_2$CO$_3$ (0.29 g, 2.1 mmol) and KI (68 mg, 0.41 mmol) in 40 ml DMF was heated at 90° C. overnight. After cooling to room temperature, insoluble materials were removed by filtration, and the filtrate was concentrated and purified by a basic alumina column (100% ethyl acetate→50:1 ethyl acetate/MeOH→20:1 ethyl acetate/MeOH). The product was isolated as a pale yellow solid. Yield=0.14 g, 51%.

(iv) Generating the Ascorbate Probe (pAP1OMe)

Ascorbate probe ligand (AP1OMe) was dissolved in ethyl acetate to generate a 5-mM solution. The 5-mM ascorbate probe ligand solution was aliquoted into 200 µL PCR tubes, dry completely in desiccator in vacuum for 24 hours and stored at −20° C. afterwards. Ascorbate probe ligand can be regenerated by adding DMSO into the PCR tube. 10 µL of 5 mM AP1OMe probe ligand in DMSO was mixed with 10 µL of 5 mM CuCl$_2$ in water. The solution was mixed thoroughly for 10-30 mins for complexation.

Example 8: Determining the Ascorbate Content in a Commercial Drink

Materials and Methods

The commercial drink YOU•C1000 Vitamin Lemon with vitamin C content 714 mg/100 ml was purchased from the off the shelf in Hong Kong. Ascorbic acid was purchased from Sigma-Aldrich.

(i) Preparation of Standard Curve of the pAP1

A calibration curve of ascorbic acid concentration at 1, 2, 5, 7.5, 10 µM was plotted against fluorescence intensity at 510 nm by using 5 µM pAP1 in deionized water.

(ii) Dilution of YOU•C1000 Vitamin Lemon

The YOU•C1000 was first diluted 10 times in deionized water.

(iii) Measurement

10 µL of 0.5 mM pAP1 solution was prepared and added to 900 µL of deionized water, and the solution was mixed thoroughly. 100 µL of diluted YOU•C1000 from step (ii) above was added to the solution containing pAp1 and was allowed to stand for 30 mins. After this time, a fluorescence measurement was taken. The concentration of ascorbic acid can be calculated by substituting the fluorescence intensity in the calibration curve to obtain the concentration of ascorbic acid in the diluted YOU•C1000. Each measurement was repeated 4 times.

(iv) Spiking and Recovery

Ascorbic acid in deionized water was added deliberately into the diluted YOU•C1000 to have a spike of concentration of 1 µM or 2 µM. The fluorescence measurement was taken as in step (iii). The % of Recovery was calculated by dividing the concentration difference between spiked diluted YOU•C1000 solution and non-spiked diluted YOU•C1000 with the expected ascorbic concentration spiked.

Example 9: Monitoring Ascorbate Uptake in Live Cells

Materials and Methods pAP1 was also used for optical imaging in live cells. For example, pAP1 was used to monitor the uptake of ascorbate by live HeLa cells in a confocal microscopy experiment. HeLa cells were treated with 50 µM pAP1 for 30 min. Another set of HeLa cells was treated with 1 mM ascorbic acid for 40 min and then 50 µM of pAP1 for 30 min.

Results

Cells treated with both pAP1 and ascorbic acid displayed enhanced fluorescence, compared to cells treated only with pAP1. These results demonstrate that the metal complexes can be used with the complex cellular matrix and that they will be useful for studying ascorbate biology in live biological samples. Fluorescence was also observed in the cells treated only with pAP1, though not as enhanced as cells treated with both pAP1 and ascorbic acid. The observed fluorescence in the cells not treated with ascorbic acid is due to background fluorescence of the probe and the background fluorescence from the cell. The cells, even without ascorbate treatment, can contain an endogenous level of ascorbate that can contribute to the observed fluorescence in these cells.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A compound comprising a metal complex having the formula:

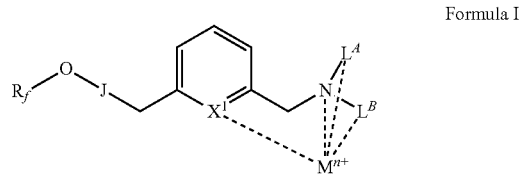

Formula I wherein:

M is a transition metal;

n is an integer between 1 and 7, inclusive;

J is a single bond capable of being cleaved by a stimulus;

R$_f$ comprises a diagnostic, therapeutic, or prophylactic agent;

L$^A$ and L$^B$ are independently CH$_2$N(R$^1$R$^2$), CH$_2$OR$^3$, CH$_2$COOR$^4$, CH$_2$SR$^5$,

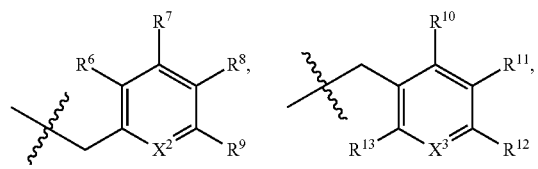

-continued

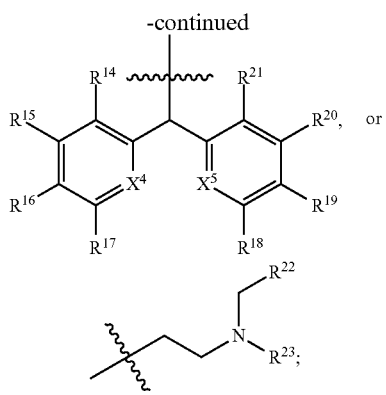

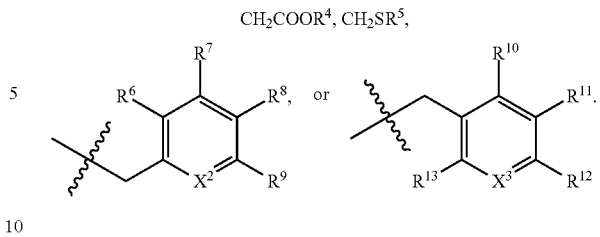

8. The compound of claim 7, wherein $R^1$-$R^{13}$ are independently hydrogen, unsubstituted alkyl, substituted alkyl, unsubstituted aryl, unsubstituted aryl, halogen, cyano, hydroxyl, unsubstituted alkoxy, substituted alkoxy, unsubstituted amino, substituted amino, unsubstituted dialkyl amine, or substituted dialkyl amine.

$X^1$, $X^2$, $X^3$, $X^4$, and $X^5$ are independently N or $CR^{24}$;

$R^1$-$R^{24}$ are independently hydrogen, unsubstituted alkyl, substituted alkyl, unsubstituted aryl, substituted aryl, unsubstituted polyaryl, substituted polyaryl, halogen, cyano, hydroxyl, unsubstituted alkoxy, substituted alkoxy, unsubstituted amino, substituted amino, unsubstituted dialkyl amine, substituted dialkyl amine, unsubstituted heteroaryl, substituted heteroaryl, unsubstituted polyheteroaryl, substituted polyheteroaryl, unsubstituted alkylthio, substituted alkylthio, unsubstituted carboxyl, substituted carboxyl, unsubstituted ester, substituted ester, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl, wherein substituents of the substituted chemical groups are selected from the group consisting of alkyl, alkenyl, alkynyl, aryl, heteroaryl, hydroxyl, alkoxy, aroxy, alkylthio, arylthio, cyano, isocyano, carbonyl, carboxyl, amino, amido, sulfonyl, sulfonic acid, phosphoryl, phosphonyl, polyaryl, unsubstituted $C_3$-$C_{20}$ cycloalkyl, and unsubstituted heterocyclyl.

2. The compound of claim 1, wherein the stimulus is ascorbic acid, or a salt thereof.

3. The compound of claim 1 having the formula:

Formula II

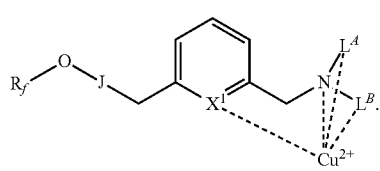

4. The compound of claim 3, wherein the diagnostic agent is a dye.

5. The compound of claim 4, wherein the dye is selected from the group consisting of a fluorescent dye, a chemiluminescent dye, a bioluminescent dye, a phosphorescent dye, or a combination thereof.

6. The compound of claim 3, wherein $X^1$, $X^2$, $X^3$, $X^4$, and $X^5$ are independently N or CH.

7. The compound of claim 3, wherein $L^A$ is $CH_2NR^1R^2$, $CH_2OR^3$,

9. The compound of claim 8, wherein $R^1$-$R^5$ are independently hydrogen, unsubstituted alkyl, substituted alkyl, unsubstituted aryl, or unsubstituted aryl.

10. The compound of claim 9, wherein $R^1$-$R^5$ are independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, or 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

11. The compound of claim 10, wherein $R^6$-$R^{21}$ are independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, F, Cl, Br, I, CN, OH, OMe, $NH_2$, or $NMe_2$.

12. The compound of claim 3, wherein $L^B$ is $CH_2N(R^1R^2)$, $CH_2OR^3$,

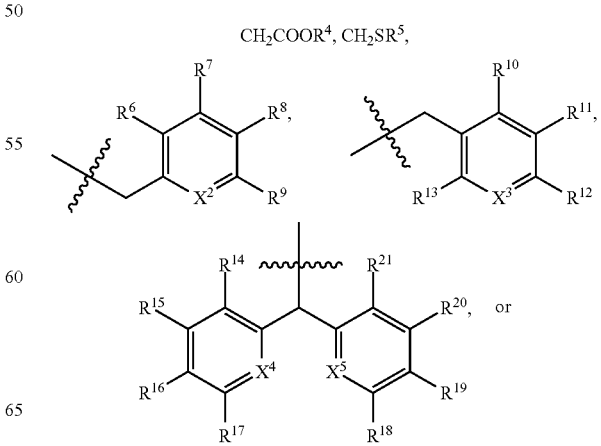

-continued

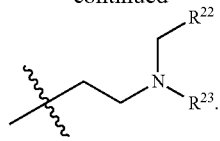

13. The compound of claim 12, wherein $R^1$-$R^{23}$ are independently hydrogen, unsubstituted alkyl, substituted alkyl, unsubstituted aryl, substituted aryl, halogen, cyano, hydroxyl, unsubstituted alkoxy, substituted alkoxy, unsubstituted amino, substituted amino, unsubstituted dialkyl amine, substituted dialkyl amine, unsubstituted heteroaryl, substituted heteroaryl, unsubstituted alkylthio, substituted alkylthio, unsubstituted carboxyl, substituted carboxyl, unsubstituted ester, or substituted ester.

14. The compound of claim 13, wherein $R^1$-$R^5$ are independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, or 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

15. The compound of claim 14, wherein $R^6$-$R^{21}$ are independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, F, Cl, Br, I, CN, OH, OMe, $NH_2$, or $NMe_2$.

16. The compound of claim 15, wherein $R^{22}$ and $R^{23}$ are independently hydrogen, methyl, ethyl, n-propyl, iso-propyl, n-butyl, sec-butyl, tert-butyl, n-pentyl, iso-pentyl, n-hexyl, phenyl, 1-napthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, F, Cl, Br, I, CN, OH, OMe, $NH_2$, or $NMe_2$, $NEt_2$, 2-pyridyl, methylthio, ethylthio, COOH, $COOR^{25}$, wherein $R^{25}$ is unsubstituted alkyl, substituted alkyl, unsubstituted aryl, or unsubstituted aryl.

17. The compound of claim 4, wherein the dye has the formula:

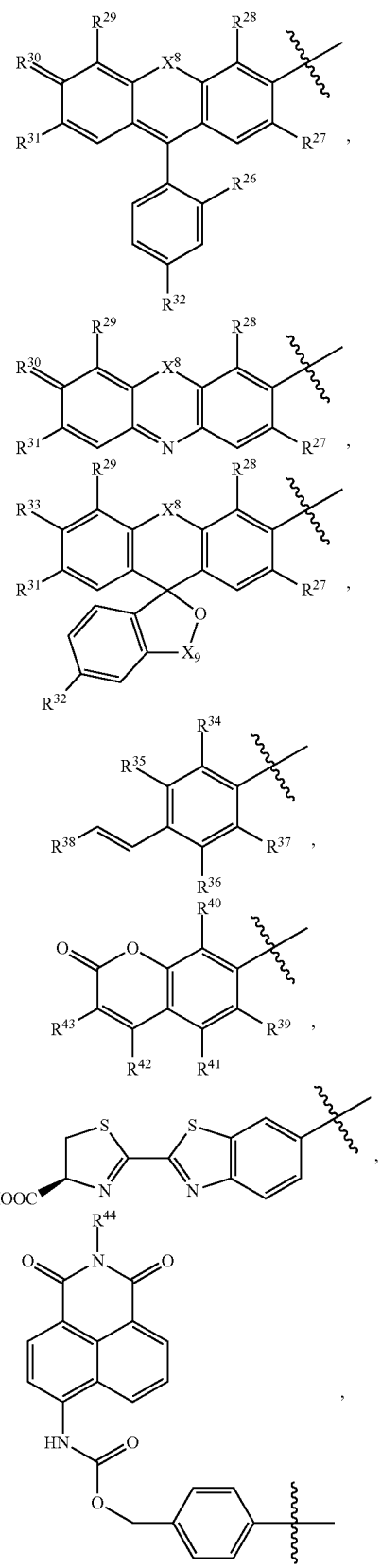

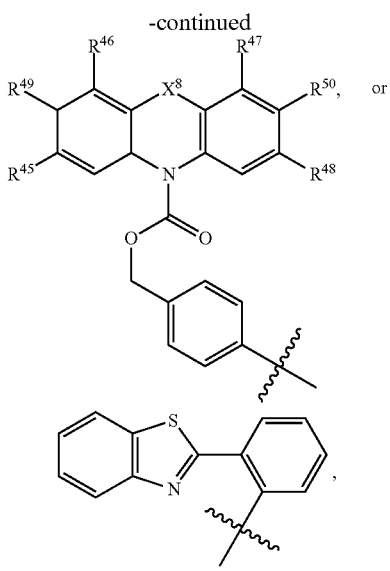

wherein:

X⁸ is O, S, Se, Te, C(R⁵²R⁵³), Si(R⁵²R⁵³), or B(R⁵²R⁵³);

X⁹ is CH₂, or C(O); and

R²⁶-R⁵³ are independently hydrogen, unsubstituted alkyl, substituted alkyl, unsubstituted aryl, substituted aryl, unsubstituted polyheteroaryl, substituted polyheteroaryl, halogen, sulfate, sulfonate, sulfamoyl, sulfonamido, sulfonyl, O, cyano, hydroxyl, unsubstituted alkoxy, substituted alkoxy, unsubstituted amino, substituted amino, unsubstituted amido, substituted amido, unsubstituted dialkyl amine, substituted dialkyl amine, unsubstituted heteroaryl, substituted heteroaryl, unsubstituted alkylthio, substituted alkylthio, unsubstituted carboxyl, substituted carboxyl, unsubstituted ester, or substituted ester.

18. The compound of claim 17, wherein X⁸ is O.

19. The compound of claim 17, wherein R⁵² and R⁵³ are independently hydrogen, unsubstituted alkyl, substituted alkyl, unsubstituted aryl, or substituted aryl.

20. The compound of claim 17, wherein R²⁶-R²⁹ and R³¹-R³² are independently hydrogen, halogen, sulfate, sulfonate, sulfonyl, unsubstituted alkyl, or substituted alkyl.

21. The compound of claim 20, wherein R²⁶-R²⁹ and R³¹-R³² are independently hydrogen, H, Cl, Br, I, SO₃H, or unsubstituted alkyl.

22. The compound of claim 17, wherein R³⁰ is O, unsubstituted amino, substituted amino, substituted dialkyl amine, or unsubstituted dialkyl amine.

23. The compound of claim 22, wherein R³⁰ is O, NH₂, or unsubstituted dialkylamine.

24. The compound of claim 17, wherein R³² is hydrogen, unsubstituted alkoxy, substituted alkoxy, unsubstituted carboxyl, substituted carboxyl, unsubstituted ester, substituted ester, unsubstituted alkyl, substituted alkyl, unsubstituted amido, substituted amido, sulfate, or sulfonate.

25. The compound of claim 24, wherein R³² is hydrogen, OR⁵⁴, COOH, COOR⁵⁴, unsubstituted alkyl, C(O)N(R⁵⁴R⁵⁵), NR⁵⁴C(O)R⁵⁵, SO₃H, wherein R⁵⁴ and R⁵⁵ are independently hydrogen, unsubstituted alkyl, substituted alkyl, unsubstituted aryl, or unsubstituted aryl.

26. The compound of claim 17, wherein R³³-R³⁷ are independently hydrogen, halogen, unsubstituted alkoxy, substituted alkoxy, unsubstituted carboxyl, substituted carboxyl, unsubstituted ester, substituted ester, unsubstituted alkyl, substituted alkyl, unsubstituted amido, substituted amido, sulfate, or sulfonate.

27. The compound of claim 26, wherein R³³-R³⁷ are independently hydrogen, F, Cl, Br, I, OR⁵⁴, COOH, COOR⁵⁴, unsubstituted alkyl, C(O)N(R⁵⁴R⁵⁵), NR⁵⁴C(O)R⁵⁵, or SO₃H, wherein R⁵⁴ and R⁵⁵ are independently hydrogen, unsubstituted alkyl, substituted alkyl, unsubstituted aryl, or unsubstituted aryl.

28. The compound of claim 27, wherein R³⁸ is

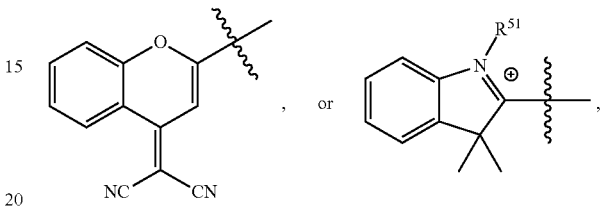

wherein R⁵¹ is unsubstituted alkyl, or substituted alkyl.

29. The compound of claim 17, wherein R³⁹-R⁴³ are independently hydrogen, halogen, unsubstituted alkoxy, substituted alkoxy, unsubstituted carboxyl, substituted carboxyl, unsubstituted ester, substituted ester, unsubstituted alkyl, substituted alkyl, unsubstituted aryl, substituted aryl, unsubstituted polyheteroaryl, substituted polyheteroaryl, unsubstituted amido, substituted amido, sulfate, or sulfonate.

30. The compound of claim 29, wherein R³⁹-R⁴³ are independently hydrogen, F, Cl, Br, I, OR⁵⁴, COOH, COOR⁵⁴, unsubstituted alkyl, C(O)N(R⁵⁴R⁵⁵), NR⁵⁴C(O)R⁵⁵, SO₃H, or

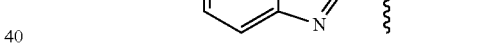

wherein R⁵⁴ and R⁵⁵ are independently hydrogen, unsubstituted alkyl, substituted alkyl, unsubstituted aryl, or unsubstituted aryl.

31. The compound of claim 17, wherein R⁴⁴ is hydrogen, halogen, unsubstituted alkoxy, substituted alkoxy, unsubstituted carboxyl, substituted carboxyl, unsubstituted ester, substituted ester, unsubstituted alkyl, substituted alkyl, unsubstituted amido, substituted amido, sulfate, or sulfonate.

32. The compound of claim 31, wherein R⁴⁴ is hydrogen, F, Cl, Br, I, OR⁵⁴, COOH, COOR⁵⁴, unsubstituted alkyl, C(O)N(R⁵⁴R⁵⁵), NR⁵⁴C(O)R⁵⁵, or SO₃H, wherein R⁵⁴ and R⁵⁵ are independently hydrogen, unsubstituted alkyl, substituted alkyl, unsubstituted aryl, or unsubstituted aryl.

33. The compound of claim 17, wherein R⁴⁵-R⁴⁸ are independently hydrogen, halogen, unsubstituted alkyl, substituted alkyl, sulfate, or sulfonate.

34. The compound of claim 33, wherein R⁴⁵-R⁴⁸ are independently hydrogen, F, Cl, Br, I, SO₃H, unsubstituted alkyl, or substituted alkyl.

35. The compound of claim 17, wherein R⁴⁹-R⁵⁰ are independently hydrogen, halogen, unsubstituted alkoxy, substituted alkoxy, unsubstituted carboxyl, substituted carboxyl, unsubstituted ester, substituted ester, unsubstituted alkyl, substituted alkyl, unsubstituted amido, substituted amido, sulfate, or sulfonate.

36. The compound of claim 35, wherein $R^{49}$-$R^{50}$ are independently hydrogen, F, Cl, Br, I, $OR^{54}$, COOH, $COOR^{54}$, unsubstituted alkyl, $C(O)N(R^{54}R^{55})$, $NR^{54}C(O)R^{55}$, or $SO_3H$, wherein $R^{54}$ and $R^{55}$ are independently hydrogen, unsubstituted alkyl, substituted alkyl, unsubstituted aryl, or unsubstituted aryl.
37. The compound of claim 1, selected from:
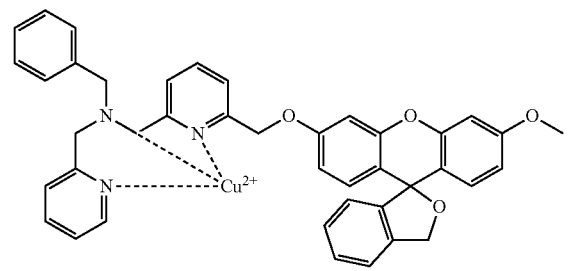
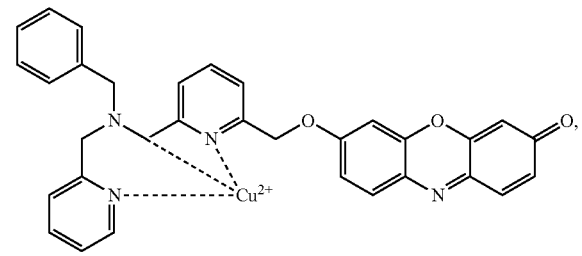
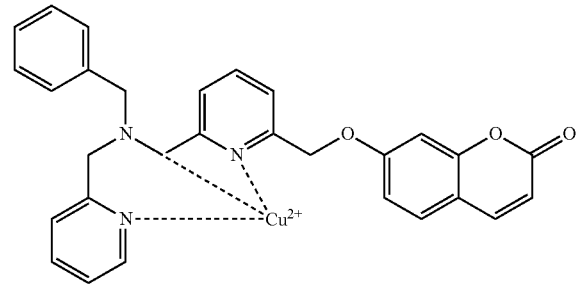
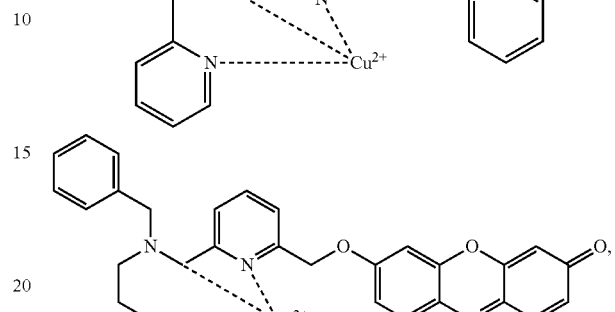
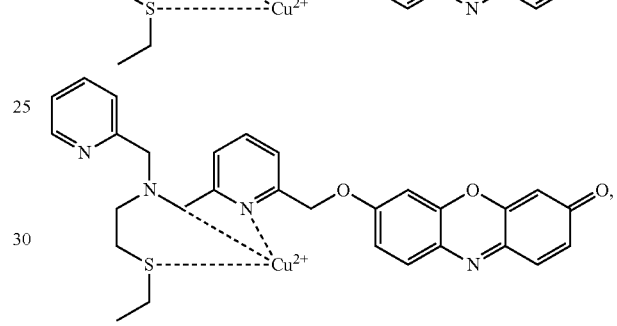
and
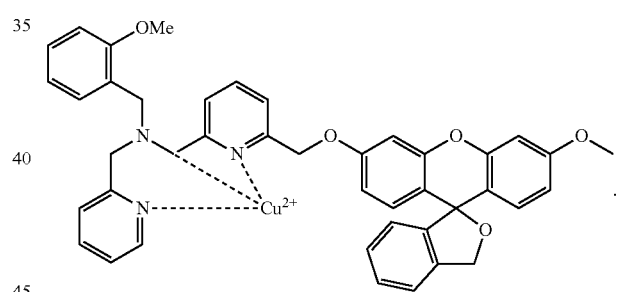
* * * * *